US012755835B1

(12) United States Patent
Arkoff et al.

(10) Patent No.: US 12,755,835 B1
(45) Date of Patent: Oct. 6, 2026

(54) AI READY SMART IV POLE SYSTEM INCLUDING MODULAR HUB FOR CLINICAL DATA INTEGRATION, COMPLIANCE AND PATIENT SERVICES

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/352,312

(22) Filed: Oct. 7, 2025

Related U.S. Application Data

(63) Continuation-in-part of application No. 19/229,627, filed on Jun. 5, 2025, now Pat. No. 12,445,308.

(51) Int. Cl.
*G16H 40/20* (2018.01)
*A61M 5/14* (2006.01)
*G16H 40/60* (2018.01)

(52) U.S. Cl.
CPC .......... *G16H 40/20* (2018.01); *A61M 5/1415* (2013.01); *G16H 40/60* (2018.01)

(58) Field of Classification Search
CPC ...... G16H 40/20; G16H 40/60; A61M 5/1415
See application file for complete search history.

(56) References Cited

U.S. PATENT DOCUMENTS 8,510,126 B2 * 8/2013 Martin .................. G16H 40/20 600/300
11,405,448 B1 * 8/2022 Seigneurbieux ...... H04L 65/612
2009/0112630 A1 * 4/2009 Collins, Jr. ............ G16H 40/20 705/2
2010/0082369 A1 * 4/2010 Prenelus ................ G16H 40/67 705/3
2014/0265611 A1 * 9/2014 Fern .................... A61M 5/1415 307/104
2019/0027237 A1 * 1/2019 McFarlane ............ G16H 10/60
(Continued)

*Primary Examiner* — Nam T Tran
(74) *Attorney, Agent, or Firm* — IP Consulting Group; Michael Razavi; Alfred F. Hoyte, Jr.

(57) ABSTRACT

The invention provides a compliance-governed, AI-ready hub configured to integrate artificial-intelligence computation, device communication, patient interaction, and regulated power distribution within a unified, modular platform for clinical environments. The hub includes a control unit executing governance-enforced firmware and software, a compliance subsystem maintaining a cryptographically secured ledger, and modular interfaces enabling connection to medical devices, patient-facing terminals, and external hospital networks. Patient identification is achieved through authenticated credentials such as bracelets, biometric tokens, or mobile applications, ensuring that each interaction remains traceable and policy-conformant. Power and communication are distributed through an internal backbone governed by validation and audit logic that enforce a deny-by-default posture for all data and control transactions. Through this architecture, the system provides a verifiable execution environment that unifies AI processing, clinical interoperability, and compliance assurance in a single extensible infrastructure for regulated healthcare operations.

30 Claims, 10 Drawing Sheets

(56) References Cited

U.S. PATENT DOCUMENTS

| | | | | |
|---|---|---|---|---|
| 2021/0050104 | A1* | 2/2021 | Arkoff | G16H 40/20 |
| 2021/0407645 | A1* | 12/2021 | Bazargan | G16H 40/60 |
| 2023/0368887 | A1* | 11/2023 | Roh | G16H 40/20 |
| 2025/0149190 | A1* | 5/2025 | Keydanskyy | G16H 40/20 |
| 2025/0202871 | A1* | 6/2025 | Choi | H04L 63/0435 |
| 2025/0293884 | A1* | 9/2025 | Gilchrist | H04L 9/3213 |

* cited by examiner

Compliance and Governance Subsystem (600)

PF-CSS

Session termination and credential revocation sequence (1000)

AI READY SMART IV POLE SYSTEM INCLUDING MODULAR HUB FOR CLINICAL DATA INTEGRATION, COMPLIANCE AND PATIENT SERVICES

CROSS-REFERENCE TO RELATED APPLICATIONS

This application claims the benefit of priority from U.S. Non-Provisional Patent Continuation in Part of application Ser. No. 19/229,627 which was filed on Jun. 5, 2025 which is a Continuation in Part of Application No of application Ser. No. 19/000,461 which is Patent #12337143 that was Issued on Jun. 24, 2025, the contents of which are incorporated herein by reference.

FIELD OF THE INVENTION

The present invention relates generally to systems and methods for integrating artificial intelligence, medical devices, and patient-facing digital services within regulated healthcare environments. More particularly, the invention pertains to a compliance-controlled, AI-ready hardware and software hub configured to deliver power, communication, data exchange, and governance functions through a unified, modular platform.

The present invention relates to integrated medical infrastructure systems and, more particularly, to a compliance-governed AI-ready hub configured to unify artificial-intelligence processing, device communication, patient-interaction services, and regulated power distribution within a single modular platform for use in healthcare environments.

BACKGROUND OF THE INVENTION

Conventional hospital infrastructure relies on fragmented device adapters, network gateways, and standalone computing units that lack common governance, data provenance, and security assurance. Medical devices, bedside terminals, and patient engagement systems often operate on separate networks or isolated management layers, resulting in inconsistent compliance enforcement, duplicate data flows, and increased cybersecurity exposure.

Existing solutions generally provide limited interoperability between patient-facing systems and regulated clinical devices. Gateways and middleware architectures typically depend on proprietary interfaces, requiring vendor-specific integrations and manual policy configuration. As hospitals incorporate artificial-intelligence-based analytics and decision-support tools, these architectures fail to provide a verifiable, governance-controlled execution environment capable of supporting both bedside and distributed AI workloads.

Moreover, patient interaction systems-such as entertainment portals or telehealth platforms-often remain disconnected from compliance and data-validation frameworks. They may exchange personal or clinical information without alignment to institutional rulesets, thereby increasing regulatory risk under frameworks such as HIPAA, GDPR, FDA Part 820, CMS Conditions of Participation, or THE device communication profiles.

Power distribution and device connectivity further complicate this landscape. Wall-mounted power panels, adapters, and POE injectors deliver energy but lack integrated monitoring, validation, or audit mechanisms. When combined with data-bearing devices, these unverified power channels introduce potential points of failure and compliance blind spots.

Accordingly, there exists a need for a single, governance-aware infrastructure that unifies power delivery, communication, and computation with embedded compliance oversight. Such a system must support modular hardware expansion, policy-driven data validation, and secure patient association while maintaining full traceability of all operational events.

The present invention addresses these deficiencies by introducing an AI-Ready Hub-a wall- or surface-mounted modular system that integrates artificial-intelligence processing, regulated power management, patient identification, and compliance-led data exchange within a verifiable framework. By embedding governance logic directly into the control, communication, and power subsystems, the invention eliminates architectural fragmentation, enhances patient safety, and ensures that all device, user, and AI interactions conform to institutional and regulatory policy.

Existing infrastructures are siloed, relying on proprietary gateways or middleware that cannot provide unified compliance enforcement. Hospitals therefore require a single, extensible platform that consolidates medical device integration, patient-facing services, power delivery, and governance into a unified execution environment. Without such a platform, compliance with HIPAA, CMS, FDA, GDPR, and emerging interoperability standards cannot be achieved at scale.

SUMMARY OF THE INVENTION

The present invention provides an AI-Ready Hub (100) configured for installation within or on a wall of a clinical environment, functioning as an integrated, compliance-controlled platform that unifies power delivery, device interoperability, patient-facing services, and artificial-intelligence computation. The hub replaces the fragmented infrastructure of conventional medical adapters and gateways with a single, governance-aware system capable of local inference, deterministic communication, and auditable data exchange.

In various embodiments, the hub comprises a modular chassis incorporating a Power Management Subsystem (500), a Control Unit (700), and an Artificial-Intelligence Execution Environment (300) interconnected through a Logical Internal Network (850). A Modular Receptor Assembly (200) enables the attachment of interchangeable components, including Medical Device Integration Modules (220), power outlets, communication adapters, and AI accelerator units such as GPUs, TPUs, FPGAs, neuromorphic, or quantum processors. This modular architecture allows healthcare facilities to scale performance and connectivity in response to evolving clinical, regulatory, and computational requirements.

The hub further integrates a Patient Association Mechanism (400), enabling secure linkage between the hub and authenticated patient identifiers such as a Bracelet (410), Smartphone (420), or biometric credential. Once authenticated, the patient gains access to individualized digital services delivered through the Patient-Facing Information and Services Subsystem (PF-CSS 250). These services may include telehealth communication, consent management, adherence support, secure payments, or educational and entertainment content. Every patient interaction, configuration change, or device event is mediated by governance tokens and recorded as a compliance-controlled ledger entry within the Compliance and Governance Subsystem (600/780).

The governance subsystem enforces a deny-by-default policy, permitting data exchange or control only after validation against rules stored in a Policy Store (612). Validated events are cryptographically signed, anchored to an immutable ledger or blockchain structure, and continuously monitored through an audit feedback loop. This framework ensures full traceability, privacy protection, and continuous regulatory conformance across hospital, regional, or federated networks. The hub's communication infrastructure-including short-range, private, and wide-area networking layers-maintains secure interoperability with hospital Wi-Fi, 5 G, and cloud-connected Electronic Health Record (EHR) systems under the same compliance regime.

Through this architecture, the AI-Ready Hub establishes a validated execution environment for bedside and distributed AI workloads, integrating computation, power, patient interaction, and governance enforcement within a single extensible platform. The invention thereby bridges clinical safety, operational efficiency, and patient-centric digital engagement, providing a scalable and regulation-compliant foundation for next-generation intelligent healthcare infrastructure.

DETAILED DESCRIPTION OF THE INVENTION

The following description sets forth the architecture, components, and operational methods of the AI-ready hub, with reference to its hardware subsystems, governance framework, patient-association mechanisms, and example use cases. The embodiments described herein illustrate the scope of the invention and provide enabling support for the claims, while recognizing that variations and equivalents may be adopted without departing from the compliance-controlled architecture disclosed.

The present invention provides an AI-ready hub configured for installation within or on a wall of a healthcare environment. The hub functions as a unified, compliance-controlled infrastructure platform integrating medical device connectivity, patient-facing information and service interfaces, communication and networking subsystems, power delivery, and governance assurance. The architecture enables bedside and remote execution of artificial-intelligence workloads while maintaining cryptographic provenance and regulatory auditability.

Definitions

AI-Ready Hub (100)

Figure 1:
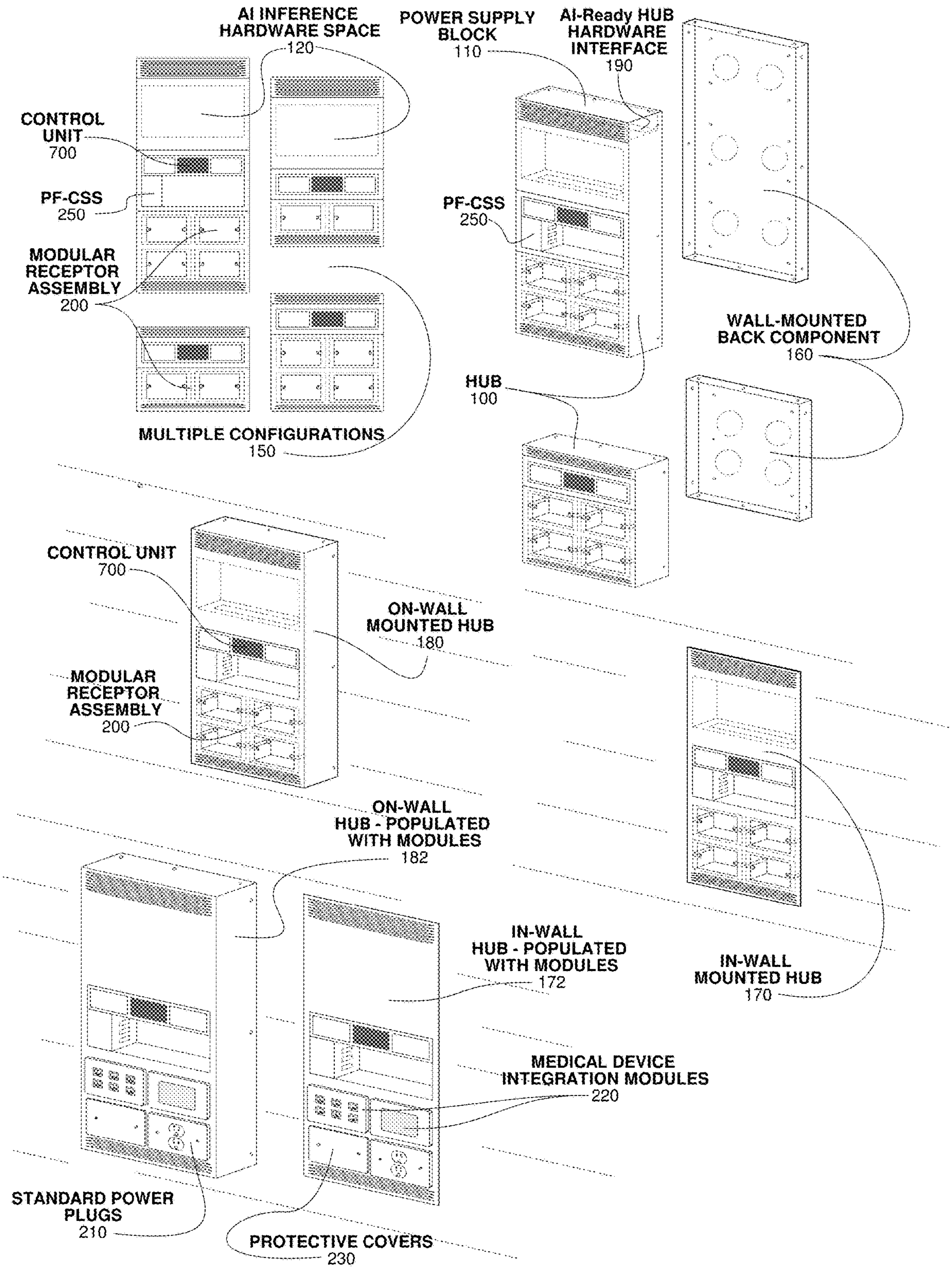
FIG. 1 illustrates the overall physical configuration of the AI-Ready Hub (100), showing its modular construction, wall- or surface-mounted embodiments, and arrangement of core subsystems including the Power Management Subsystem (500), Control Unit (700), AI Execution Environment (300), and Patient-Facing Information and Services Subsystem (PF-CSS 250).
Figure 2:
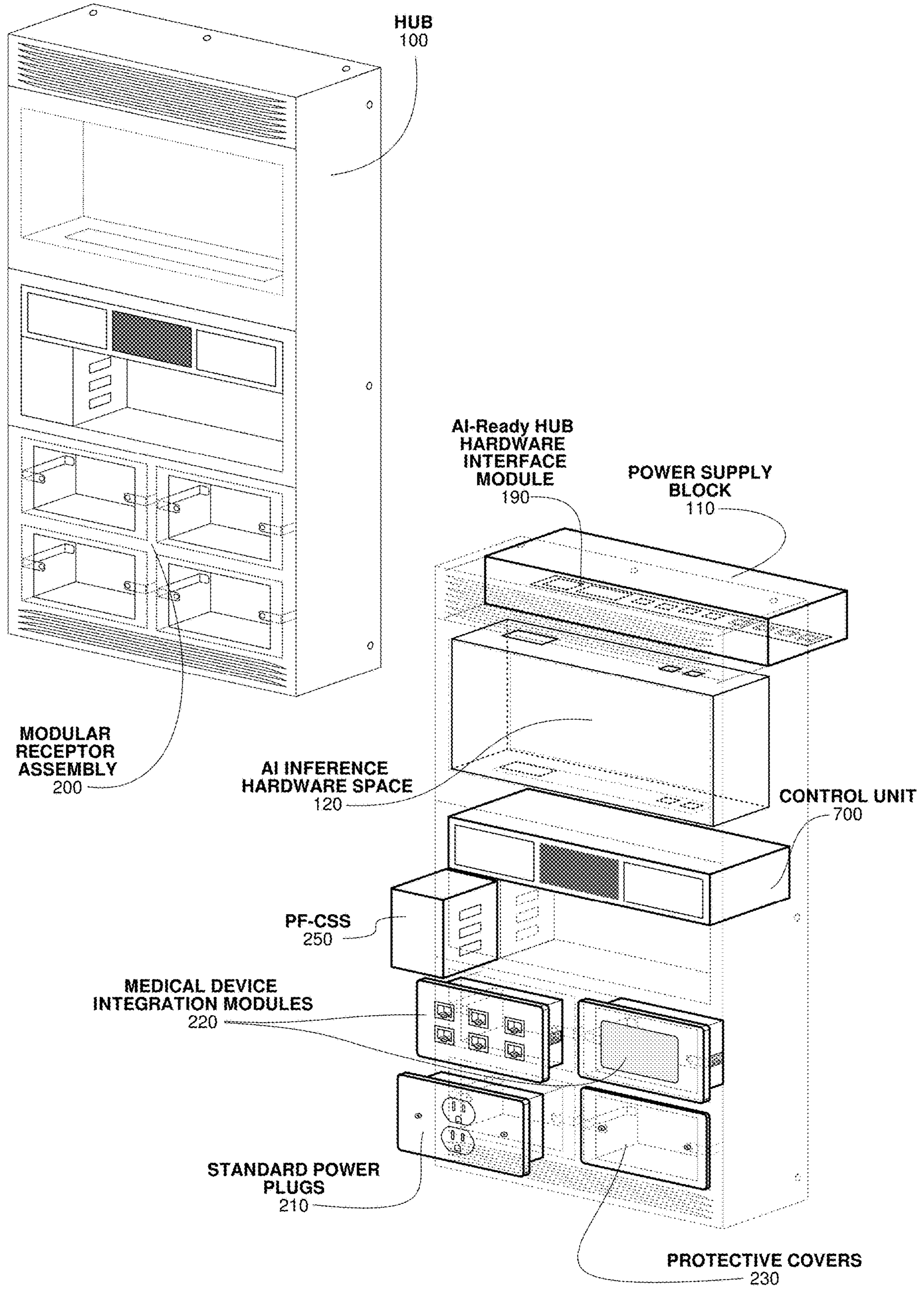
FIG. 2 depicts an exploded structural view of the AI-Ready Hub (100), highlighting the interrelation between the Power Supply Block (110), AI-Ready Hub Hardware Interface Module (190), Control Unit (700), Medical Device Integration Modules (220), PF-CSS (250), and protective cover assemblies.

Referring now to FIGS. 1 and 2, the AI-Ready Hub (100) is an integrated, wall-mounted or surface-mounted clinical hardware platform configured for use in regulated healthcare environments. The hub provides localized execution of artificial-intelligence workloads and deterministic management of power, communication, and compliance operations across connected medical and patient-facing systems within a governance-controlled infrastructure.

The hub includes a modular chassis with standardized mounting configurations (170-182) and houses a mandatory Power Management Subsystem (500) forming the electrical and network backbone of the device. Integrated within the power subsystem is the AI-Ready Hub Hardware Interface Module (190), which acts as the fixed ingress connector for both power and data, supporting Power-over-Ethernet (POE), USB-C, and AC mains inputs with galvanic isolation in compliance with IEC 60601-1. The Control Unit (700) serves as the orchestration processor and hosts the AI-Ready Hub Software Interface Module (795), which governs interoperability, discovery, and policy enforcement across the internal backbone established by module (190).

Through secure protocol exchanges, the Software Interface Module (795) supervises the Hardware Interface Module (190) to coordinate power-state transitions, link authentication, and compliance telemetry validated by the Compliance and Governance Subsystem (600/780). The hub further integrates at least one Modular Receptor Assembly (200) for medical device connections and may include an optional Patient-Facing Information and Services Subsystem (PF-CSS 250) embodied as a plug-in module or as an associated tablet interface coupled through the internal backbone formed by modules (190) and (795). In this configuration, the tablet operates as the primary patient-interaction surface for telehealth, consent management, and educational content generated by the AI Subsystem (340).

Each operational event-including power negotiation, network authentication, and patient interaction—is validated and recorded through the Compliance and Governance Subsystem (600/780), ensuring traceable, policy-compliant functionality. Accordingly, the AI-Ready Hub (100) functions as a unified hardware and software platform that delivers local intelligence, secure connectivity, and governance-compliant interoperability within the clinical environment.

AI-Ready Hub Hardware Interface Module (190)

The AI-Ready Hub Hardware Interface Module (190) is a fixed connector assembly integrated within the Power Management Subsystem (500). It serves as the hub's combined electrical and network ingress point, managing input from PoE, USB-C, or AC sources and providing isolation pathways compliant with IEC 60601-1. The module establishes the internal backbone that simultaneously distributes regulated power and digital communication among all connected subsystems, forming the physical layer of the hub's unified infrastructure.

The Hardware Interface Module (190) enables modular attachment of patient-facing or network-connected devices-such as PF-CSS tablets, medical-device modules, or AI components-without additional adapters. It performs dynamic power negotiation, isolation switching, and secure data-channel initialization under governance control, ensuring both electrical safety and network integrity. Operational status, source authentication, and telemetry data from module (190) are transmitted to the AI-Ready Hub Software Interface Module (795) for coordination and to the Compliance and Governance Subsystem (600/780) for event logging.

Through this integration, module (190) provides a seamless, compliance-enforced backbone that unifies energy delivery and digital connectivity within the hub's mandatory power subsystem.

AI-Ready Hub Software Interface Module (795)

The AI-Ready Hub Software Interface Module (795) executes within the Control Unit (700) and serves as the logical coordination layer governing interoperability, discovery, and command routing among all subsystems of the hub. It supervises and manages operations of the AI-Ready Hub Hardware Interface Module (190), including authentication, encryption, and real-time power-state synchronization across the internal backbone.

The Software Interface Module (795) exposes secure interfaces for device discovery, firmware negotiation, and metadata exchange between hub subsystems and external systems such as electronic medical record (EMR) servers, picture archiving and communication systems (PACS), or distributed AI inference environments. It enforces governance-token and policy-based access controls to ensure that every data exchange, driver update, and configuration operation remains compliant with institutional and regulatory policies.

All validation, configuration, and execution events processed by the Software Interface Module (795) are recorded as compliance-controlled ledger entries through the Compliance and Governance Subsystem (600/780), providing full traceability, accountability, and auditability of all power and data exchanges within the AI-Ready Hub (100). The cooperative operation of modules (190) and (795) thereby establishes a secure, modular framework enabling deterministic, policy-constrained interoperability within a clinical network environment.

Back Component (160)

A structural mounting plate or mechanical adapter configured to affix the Hub (100) to a wall surface when in-wall installation is not feasible. The back component maintains mechanical stability, compliance isolation, and supports the modular stacking of subsystems as illustrated in FIG. 1.

Modular Receptor Assembly

A standardized section of the hub chassis providing one or more keyed outlet spaces capable of accepting interchangeable modules, including medical-device integration modules, standard electrical-outlet modules, nurse-call modules, or protective covers.

It has two or more outlet spaces mechanically and electrically adapted to accept interchangeable modules. Acceptable modules include, without limitation:

(a) medical-data integration modules;
(b) standard electrical outlet modules compliant with regional norms such as Schuko or NEMA;
(c) nurse-call or functionally equivalent signaling modules;
(d) artificial-intelligence accelerator modules; and
(e) protective covers that maintain ingress protection when unused.

Module/Interchangeable Module

A module or interchangeable module denotes a discrete hardware unit insertable into the modular receptor assembly, mechanically retained and electronically authenticated by the governance subsystem. Each module bears a descriptor identifying its function, firmware, and certification state recorded in the compliance ledger.

Artificial-Intelligence Accelerator Module

A hardware or firmware unit optimized for executing artificial-intelligence or machine-learning workloads. The module may include GPUs, TPUs, FPGAs, ASICs, neuromorphic or quantum processors, or successors thereof. It operates within the patient-care boundary under governance-token authorization, reporting execution results to the compliance ledger.

Distributed or Delegated Inference

Refers to the process by which an artificial-intelligence execution environment dynamically offloads model execution or partial model computation to remote, federated, or cloud-based resources under governance control. The delegation decision may be based on resource availability, latency, policy rules, or workload balancing. Returned results are verified, cryptographically signed, and recorded within the compliance ledger to preserve the same audit and governance guarantees as local execution.

Nurse-Call Module or Equivalent Signaling Module

A nurse-call module or equivalent signaling module refers to a plug-in or embedded unit that provides manual or automated signaling to summon clinical assistance or generate alarm notifications. The term includes wired or wireless implementations interoperable with hospital nurse-call infrastructure or equivalent clinical-alert systems. Activation events are recorded as compliance-controlled ledger entries.

Control Unit

A control unit comprises at least one processor, memory, and non-transitory storage executing instructions that coordinate medical-device integration, patient-facing subsystems, artificial-intelligence operations, power management, and compliance enforcement. The control unit provides the logical and computational core of the hub and maintains bidirectional communication with all subsystems.

Power Subsystem/Power-Management Subsystem

The power subsystem (or power-management subsystem) supplies regulated electrical energy to internal and external components. It supports Power-over-Ethernet (POE, PoE++), high-power USB-C, and future delivery standards. It monitors voltage, current, thermal conditions, and load, generating compliance-ledger entries upon anomaly detection.

Passive Thermal Management (580)

A thermal dissipation structure integrated within the Power Management Subsystem (500) that employs conduction and convection pathways to maintain operational temperatures without active fans or pumps.

Medical-Device Subsystem

The medical-device subsystem encompasses one or more medical-data integration modules and interfaces that connect infusion pumps, monitors, laboratory analyzers, and sensors to the hub. Data from this subsystem is normalized and validated under governance control.

Artificial-Intelligence Subsystem

The artificial-intelligence subsystem includes the Artificial-Intelligence Execution Environment and associated accelerator hardware executing AI or machine-learning models. It performs inference, trend analysis, or safety prediction under cryptographic governance.

Patient-Facing Subsystem (PF-CSS)

The patient-facing subsystem, or patient-facing information and services subsystem (PF-CSS), denotes the portion of the hub or attached tablet that delivers interactive services—telehealth, consent, adherence, education, secure payments, and entertainment—to authenticated patients. Operation is permitted only upon issuance of a valid governance token.

Artificial-Intelligence Execution Environment

Artificial-Intelligence Execution Environment is the physical and logical domain within the hub hosting accelerator hardware, dedicated power connectors, and high-speed network interfaces, forming the secure enclave in which AI workloads are executed under compliance supervision.

Compliance Ledger

A compliance ledger is a tamper-evident data store that records validation, access, configuration, and audit events generated by the governance subsystem. Entries contain provenance fields identifying subsystem, timebase, and policy version, and may be anchored to a blockchain or distributed-ledger network for immutability.

Governance Subsystem

The governance subsystem enforces compliance policies, issues governance tokens, validates all operations, maintains the compliance ledger, and performs cryptographic signing of events locally or across federated networks.

Governance Token

A governance token is a cryptographically generated authorization artifact defining the scope, lifetime, and conditions of an approved operation-such as data release, service activation, or power control. All token issuances, uses, and revocations are ledgered.

Compliance-Controlled Event

A compliance-controlled event denotes any transaction or operation—data validation, AI inference, credential issuance, or patient interaction—that is recorded in the compliance ledger and cannot proceed absent governance token authorization.

Governance Policy Store

A governance policy store is a repository of digital policy objects specifying validation criteria, data-handling rules, and release conditions applied by the governance subsystem.

Communication Endpoint (470)

Figure 4:
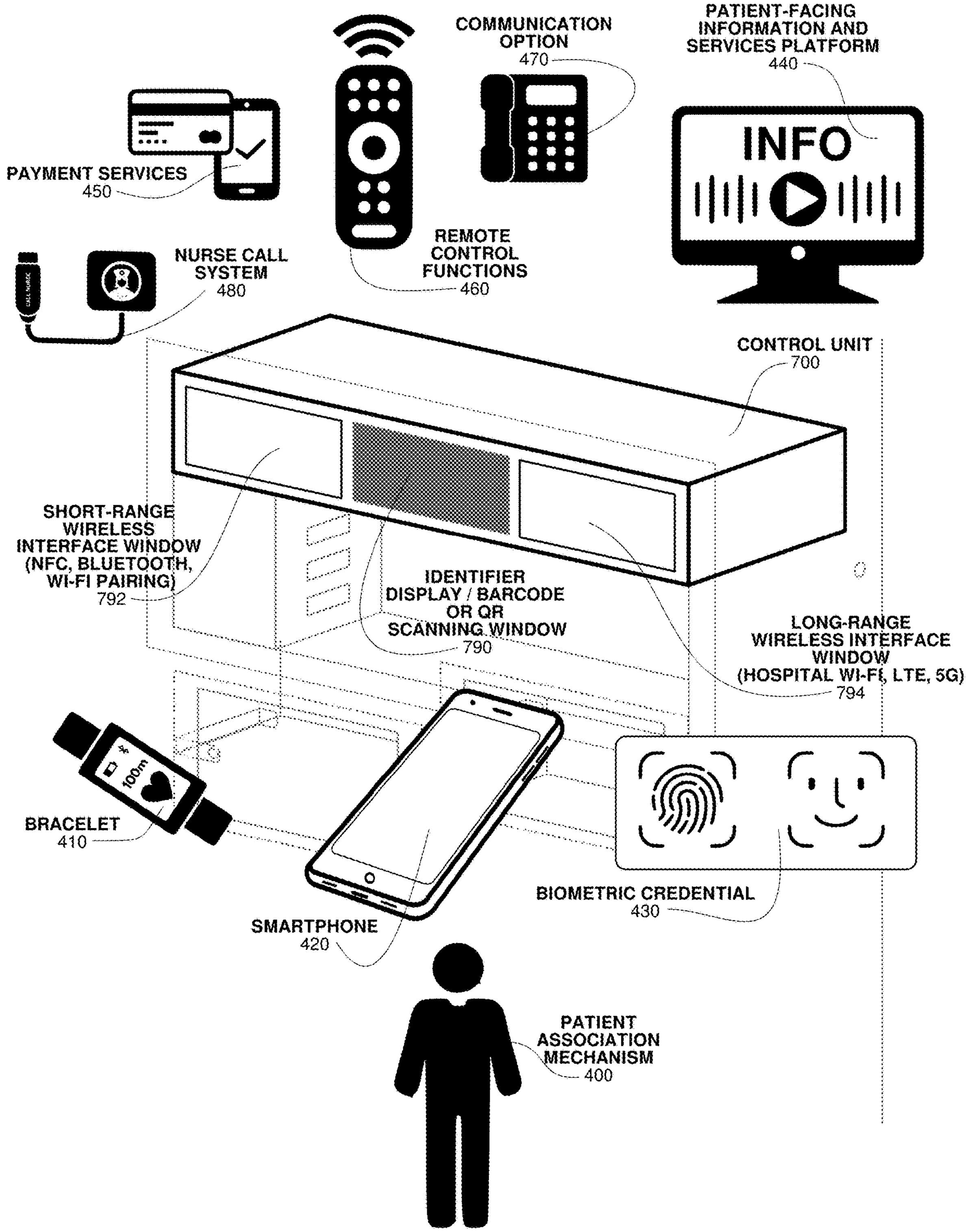
FIG. 4 presents the Patient Association Mechanism (400) and its integration with the Control Unit (700). The figure demonstrates the use of identifiers such as the Bracelet (410), Smartphone (420), Biometric Credential (430), and related communication interfaces (790, 792, 794) to establish secure patient identity linkage under compliance control.
Figure 9:
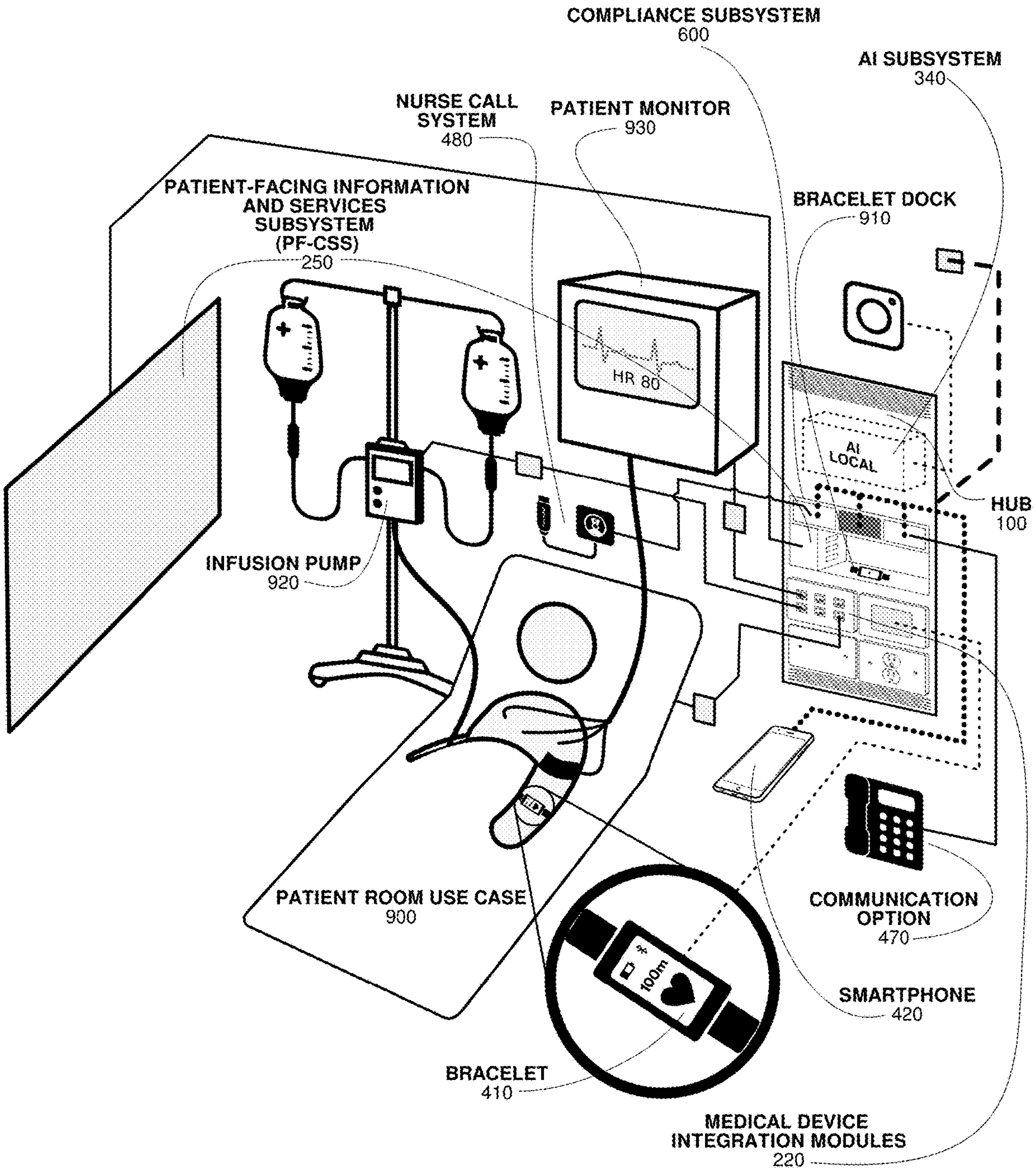
FIG. 9 presents a representative Patient Room Use Case (900), illustrating how the AI-Ready Hub (100) integrates with bedside devices such as the Infusion Pump (920) and Patient Monitor (930), as well as the PF-CSS (250), Nurse Call System (480), Bracelet Dock (910), and patient identifiers (410, 420, 470) under continuous compliance supervision.

A telecommunication or intercom endpoint associated with the Hub (100), enabling bidirectional voice or data communication between patients and staff, as depicted in FIG. 4 and FIG. 9. May include VOIP, SIP, or dedicated hospital handset integration.

Federated Governance Network

A federated governance network is a plurality of hubs or institutional nodes that synchronize compliance-ledger subsets to achieve distributed validation, cross-site auditability, and harmonized policy enforcement while preserving local data sovereignty.

Federated Governance Network

A federated governance network is a plurality of hubs or institutional nodes that synchronize compliance-ledger subsets to achieve distributed validation, cross-site auditability, and harmonized policy enforcement while preserving local data sovereignty.

Distributed Validation

Distributed validation refers to the process by which compliance verification, policy enforcement, and data authentication are shared, replicated, or collaboratively executed among multiple nodes or subsystems within a federated governance network. The process ensures mutual consistency of compliance records, eliminates single points of verification failure, and enables validation to occur across institutional, regional, or cross-provider infrastructures while maintaining audit integrity and regulatory accountability.

Longitudinal Compliance Assurance

Longitudinal compliance assurance refers to the capability of maintaining continuous, traceable, and policy-consistent auditability of compliance events and governance activities over time and across multiple locations or operational contexts. It ensures that compliance integrity is preserved throughout the lifecycle of validated events, even as policies evolve or systems are redeployed, by linking compliance-ledger entries, cryptographic signatures, and governance tokens in a verifiable temporal sequence.

Hardware Security Module (HSM)

A hardware security module is a tamper-resistant cryptographic element embedded in the hub for key management, token signing, and ledger attestation. Each invocation produces an auditable ledger entry confirming hardware integrity.

Secure Timebase

A secure timebase refers to a clock or timing mechanism synchronized via authenticated NTP, PTP, or GNSS signals, used to generate cryptographically verifiable timestamps bound to ledger entries.

Provenance Field

A provenance field is a structured metadata element embedded within a ledger record identifying the origin device, operator, policy version, and optional blockchain-anchor reference of the corresponding event.

Patient Association Mechanism

A patient association mechanism includes hardware and software elements that authenticate and bind a patient identifier to the hub, such as bracelets, smartphones, or biometric credentials, thereby enabling personalized services and data partitioning.

Bracelet/Wearable Bracelet

A bracelet or wearable bracelet denotes a patient-specific identifier device equipped with wireless communication (e.g., BLE, RFID, NFC) used for secure association, location tracking, and credential activation with the hub.

Predictive Maintenance

Predictive maintenance means the use of analytics or machine-learning models to detect abnormal patterns in power consumption, thermal load, or subsystem metrics, predicting potential failure and generating corresponding ledger entries. The analysis of operational data such as power consumption, thermal load, and subsystem performance to forecast potential failures, trigger alerts, and create ledger entries supporting proactive service or component replacement.

Deny-by-Default Gate/Release Posture

A deny-by-default gate is a governance mechanism that blocks any data or control command until validation succeeds under active policy conditions. The release posture defines this operational stance system-wide.

A control mechanism enforcing zero-trust access within the Compliance and Governance Subsystem (600), ensuring that only explicitly authorized data transactions are permitted, with all other requests automatically denied.

Compliance-Controlled Power Delivery

Compliance-controlled power delivery means regulated electrical supply monitored and logged by the governance subsystem, ensuring that every power event has an auditable record.

Real-Time Location Service (RTLS)

A real-time location service utilizes BLE, UWB, RFID, or equivalent technologies to associate devices, patients, or assets with spatial coordinates, each update forming a ledgered event.

Patient-Facing Credential Revocation

Patient-facing credential revocation describes the automatic deletion or invalidation of patient credentials upon bracelet disassociation, discharge, or policy expiration, with each revocation logged.

Break-Glass Mode

Break-glass mode designates an emergency override permitting temporary bypass of standard authentication for urgent clinical intervention. Activation requires dual authorization and produces an immutable ledger record identifying actors, timestamps, and justification.

Hybrid Cloud Inference

Hybrid cloud inference refers to coordinated execution of AI models between local accelerator hardware and remote cloud resources, wherein both outputs are cryptographically validated and recorded in the ledger to preserve compliance parity.

Edge-Level Federated Learning

Edge-level federated learning describes distributed training across multiple hubs in which encrypted model updates—not raw data—are exchanged under governance supervision and ledger logging.

Mesh Networking

Mesh networking means a peer-to-peer interconnection of hubs forming a self-healing network fabric that relays only validated and signed packets, each relay producing a ledger entry.

Predictive Communication

Predictive communication is the anticipatory routing or caching of data to preserve validated connectivity during network degradation, executed under governance-token control and logged as a compliance-controlled event.

Governance-Controlled AR/VR Visualization

Governance-controlled AR/VR visualization denotes augmented- or virtual-reality rendering of validated clinical data permitted only upon issuance of a governance token and cryptographically logged in the ledger.

AI Explainability Manifest

An AI explainability manifest is metadata attached to an AI model or inference output documenting dataset lineage, validation metrics, and model version identifiers, stored alongside corresponding ledger entries.

Compliance-Controlled Telehealth Session

A compliance-controlled telehealth session is any interactive clinical communication initiated through the hub or PF-CSS under governance-token authorization and recorded in the compliance ledger for auditability.

Governance-Controlled Software Development Kit (SDK)

A governance-controlled SDK is a certified development framework permitting third-party module or software creation under compliance supervision. Each build or deployment is cryptographically signed and ledgered before activation.

Certification and Signing Process

The certification and signing process encompasses validation, code review, and digital-signature application steps required before any third-party module or firmware becomes operational within the hub. Certification metadata are permanently recorded in the compliance ledger.

Non-Transitory Computer-Readable Medium

A non-transitory computer-readable medium includes any physical memory device—such as flash, ROM, EEPROM, or magnetic or optical storage—that stores executable instructions which, when executed by the hub's processor, cause the hub to perform the described functions.

Compliance-Controlled Audit Trail

A compliance-controlled audit trail means the complete chronological set of ledgered events providing verifiable provenance for all hub operations, accessible only under governance-token authorization.

Federated Compliance Synchronization

Federated compliance synchronization refers to cryptographically signed replication of ledger subsets among multiple hubs or governance nodes to achieve distributed consensus and immutable cross-site auditability.

Healthcare Environment

A healthcare environment refers to any physical or virtual setting in which clinical care, patient monitoring, or medical data exchange occurs, including hospitals, clinics, outpatient facilities, nursing or rehabilitation centers, and home-care or remote-care sites.

The term expressly includes locations where the hub is installed for use by licensed healthcare personnel or under institutional governance, and encompasses associated digital infrastructure such as hospital information systems, electronic medical records (EMR/EHR) servers, and secure clinical networks.

Use of the term does not limit the invention to any specific building type or regulatory jurisdiction.

The term encompasses hospitals, clinics, laboratories, rehabilitation centers, home-care environments, and any remote or hybrid care setting participating in or capable of participating in a federated governance network.

Local Artificial-Intelligence Execution

Local artificial-intelligence execution means the performance of inference, analytics, or machine-learning tasks by hardware physically located within the hub or within its immediate network boundary, as opposed to remote or cloud-based processing.

Local execution utilizes the hub's dedicated AI-hardware circuitry and control unit to process patient-associated or device-generated data under compliance governance.

Results of such execution are recorded as compliance-controlled events in the ledger, ensuring that all AI outputs remain subject to institutional policies and audit mechanisms.

Primary Power Module

A primary power module is the principal electrical-supply component of the hub responsible for receiving external power input and distributing regulated power to the modular chassis and its subsystems.

The primary power module supports standardized delivery formats including Power-over-Ethernet (POE, PoE++), high-power USB-C, or successor power-delivery technologies.

It may include voltage-conversion, current-limiting, and fault-detection circuitry and communicates operating metrics-such as load, thermal status, and fault conditions—to the compliance ledger.

In modular embodiments, the primary power module may occupy one or more dedicated spaces within the hub chassis and is replaceable without altering compliance certification.

Artificial-Intelligence Subsystem

The artificial-intelligence subsystem comprises the accelerator module, Artificial-Intelligence Execution Environment, and related firmware responsible for inference, prediction, and analytical processing. It interacts with the compliance subsystem to validate outputs before release.

AI-Hardware Circuitry

Physical processors, memory, and interfaces dedicated to performing AI or machine-learning operations within the Artificial-Intelligence Execution Environment. Includes specialized logic and buses configured for high-throughput parallel computation.

Automated Network Validation

A process executed by the communication subsystem to measure and verify network performance parameters-throughput, latency, jitter, and packet-loss-against compliance thresholds, logging results in the compliance ledger.

BLE (Bluetooth Low Energy)

A short-range wireless communication protocol used for secure, low-power data exchange between the hub and peripherals such as patient bracelets or mobile devices. BLE transactions may serve as part of the patient-association mechanism or RTLS infrastructure.

Compliance-Validated Execution Environment

A computational context, either physical or virtual, in which every data flow, command, and AI inference is subject to validation, authorization, and logging by the compliance subsystem, ensuring continuous adherence to institutional governance rules.

Deny-by-Default/Deny-by-Default Gate

A security and compliance posture in which operations, data transmissions, or control commands are blocked until explicitly validated and authorized according to policy. Implemented by the governance subsystem as a logical gate protecting all outputs.

Infotainment Services

Optional patient-facing applications that provide entertainment, news, or educational content within the PF-CSS, operating only under governance-token authorization and logged as compliance-controlled events.

Location-Service Infrastructure (RTLS)

A system employing radio-frequency technologies such as BLE, UWB, or RFID to determine the physical location of patients, devices, or hubs in real time. Location metadata are associated with validated data and recorded in the compliance ledger.

Medical-Device Integration Modules

Interchangeable modules mechanically and electrically compatible with the modular receptor assembly, configured to interface medical devices, sensors, or vendor-specific systems for data acquisition, normalization, and validation.

NTP, PTP, and GNSS

Standardized time-synchronization protocols used by the secure timebase:

- NTP (Network Time Protocol) synchronizes clocks across IP networks;
- PTP (Precision Time Protocol) provides sub-millisecond synchronization for deterministic systems; and
- GNSS (Global Navigation Satellite System) includes GPS, Galileo, and equivalent constellations supplying authenticated time signals.

The hub may use any or a combination thereof for generating cryptographically verifiable timestamps.

Patient-Care Boundary

The physical and logical perimeter within which patient data are collected, processed, or displayed under clinical governance. All AI computations and device interactions occurring inside this boundary are subject to compliance validation and audit recording.

Patient-Facing Subsystem (PF-CSS)

The subsystem or connected device providing interactive interfaces to the patient for telehealth, consent, adherence, education, secure payments, and infotainment. Operation requires issuance of a governance token, and all activities are recorded as compliance-controlled events.

Performance Metrics

Quantitative indicators such as power consumption, temperature, processing load, latency, or error rates used by the control unit for predictive maintenance, quality-of-service management, and compliance logging.

Power-Over-Ethernet (POE, PoE++)

A standardized technology that delivers DC electrical power and network connectivity over a single Ethernet cable. PoE++ (IEEE 802.3bt or successors) provides higher wattage suitable for powering hub modules and connected medical devices. The power subsystem monitors these circuits and records status data in the compliance ledger.

RFID (Radio-Frequency Identification)

A communication technology using passive or active tags and readers to identify and track devices or patients. RFID signals may form part of the RTLS infrastructure or patient-association mechanism.

Standard Electrical-Outlet Modules

Removable modules providing conventional mains-power sockets compliant with regional standards such as Schuko or NEMA formats, installable in the modular receptor assembly and logged as configuration events.

Successor Power-Delivery Standards

Any future-generation electrical-power interface or protocol offering functional equivalence or improvement over PoE, PoE++, or USB-C, including but not limited to higher-power Ethernet standards or emerging DC-bus technologies. Inclusion of such successors shall not be considered a departure from the invention.

Tablet Computer

A portable computing device with a touchscreen interface that serves as a patient-facing terminal when associated with the hub. The tablet may execute hospital-authorized software and communicate securely with the compliance subsystem.

Hospital-Authorized Software

Applications digitally signed or otherwise certified by a healthcare institution or governing authority for use within the hospital network and subject to compliance-ledger monitoring. Includes PF-CSS apps and telehealth interfaces.

Secure Payments

Electronic transactions performed through the patient-facing subsystem under governance-token control, supporting medical billing, copayments, or service subscriptions. All payment sessions are logged as compliance-controlled events.

UWB (Ultra-Wideband)

A short-range, high-bandwidth radio technology capable of precise spatial positioning and distance measurement, optionally employed within the RTLS infrastructure for tracking patients or equipment.

Unified Infrastructure

The integrated combination of subsystems-medical-device, AI, patient-facing, communication, power, and compliance-operating under a single governance and control framework to provide continuous, auditable operation within the healthcare environment.

USB-C

A reversible, high-power, high-speed universal serial bus connector compliant with USB Type-C and related Power Delivery (PD) specifications, used for both data and electrical power transfer between hub modules and connected devices.

Anomalous Traffic

Network or data activity that deviates from established operational baselines, thresholds, or compliance policies. Anomalous traffic includes abnormal packet rates, unexpected destinations, or unvalidated payloads detected by the security and anomaly-detection subsystem and recorded in the compliance ledger.

Clinical Notification

An electronic or audible message generated by the hub or connected systems to inform healthcare personnel of a clinically relevant event, such as an AI-detected risk, device fault, or patient request. Clinical notifications include, but are not limited to, nurse-call alerts, on-screen warnings, or networked alerts routed through the hospital system.

Continuity of Compliance

The maintenance of uninterrupted compliance-ledger integrity and event traceability during network disruptions or hardware downtime. Validated data are cached locally and resynchronized upon reconnection so that the audit trail remains complete and tamper-evident.

Cross-Site Auditability

Cross-site auditability refers to the ability of one or more hubs, systems, or governance nodes-whether within a single healthcare institution or across multiple organizations—to mutually verify, reconcile, and authenticate compliance ledger entries, ensuring consistent validation and traceability across distributed or federated environments.

Distributed Quality-of-Service (QoS)

A resource-management framework operated by the control unit that allocates bandwidth and computational priority among connected devices and subsystems, ensuring that real-time clinical data streams receive precedence over non-critical traffic. QoS decisions and adjustments are recorded as compliance-controlled events.

Federated Governance Network

A set of interconnected hubs or governance nodes operating under common compliance protocols, wherein each node maintains a local compliance ledger and synchronizes ledger subsets with peers. This network enables distributed validation, cross-site auditability, and policy harmonization while preserving institutional autonomy.

IV Pole

A stationary or mobile medical-device platform supporting infusion pumps, sensors, and patient-monitoring devices. When networked with the hub, the IV pole becomes part of the medical-device subsystem, transmitting validated data and receiving governance-controlled alerts.

IV Pole/Smart IV Pole System

An IV pole refers to a stationary or mobile medical-device support structure designed to hold and manage infusion pumps, sensors, monitoring equipment, and associated patient-therapy devices. The term Smart IV Pole system denotes an IV pole equipped with embedded or networked electronic components enabling data acquisition, communication, and governance integration with the hub.

In certain embodiments, the Smart IV Pole system includes one or more of:

- integrated data ports, wireless transceivers, or PoE/USB-C power interfaces for device connectivity;
- local sensors measuring infusion status, fluid levels, or patient proximity;
- a communication interface linking directly to the hub or hospital network for compliance-controlled data exchange;
- capability for automatic association with a patient identifier through the patient association mechanism or bracelet;
- onboard or connected processors executing symbolic arbitration, local validation, or AI inference related to therapy delivery; and
- a governance interface for credential management, nurse-call signaling, or alarm suppression consistent with compliance policies.

The Smart IV Pole system operates as a node of the medical-device subsystem, transmitting validated device data to the hub, receiving governance-controlled commands, and generating compliance-ledger entries for each interaction. When coupled to the hub, it forms part of a unified infrastructure ensuring end-to-end traceability, power integrity, and safety compliance throughout the patient-care boundary.

Nurse-Call Alert

A specific clinical notification signal generated manually by a patient or automatically by the hub or AI subsystem (340), to request nursing assistance or escalate a condition. Each nurse-call alert is validated, transmitted to the nurse-call infrastructure, and recorded as a compliance-controlled event.

Patient Deterioration

A decline in patient physiological condition or monitored parameters—such as vital-sign deviation, infusion-pump anomaly, or sensor trend-detected by the AI subsystem (340), through predictive algorithms and validated by the compliance subsystem before triggering a clinical notification.

Patient-Facing Information

Data, visualizations, and messages presented to the patient through the PF-CSS or associated tablet, including educational material, treatment summaries, consent prompts, adherence reminders, and billing information. All patient-facing information exchanges are compliance-controlled events.

Patient Wearables and Medical Devices

Portable or body-mounted sensors, bracelets, or therapeutic devices that communicate with the hub via BLE, UWB, RFID, or wired interfaces to transmit physiological data or identity information for validation and recording in the compliance ledger.

Payment Sessions

Authenticated electronic transactions conducted through the patient-facing subsystem for medical billing, co-payments, or subscription services. Each session operates under a governance token and is logged as a compliance-controlled event containing transaction identifiers and time-stamped confirmation.

Policy Harmonization

Policy harmonization refers to the synchronization or alignment of compliance policies, validation criteria, or governance directives among multiple hubs or domains within a federated governance network, including intra-institutional and cross-provider configurations, ensuring uniform application of rules and consistent interpretation across all connected systems.

Real-Time Clinical Data

Data generated by medical devices or sensors that describe patient physiological states or therapy parameters with timing constraints such that their clinical relevance depends on immediate or near-immediate availability. The hub prioritizes transmission and validation of real-time clinical data within the distributed QoS framework.

Router or Gateway Device

A network component integrated within or associated with the hub that aggregates data from external or home-care medical devices, normalizes and validates such data, and forwards compliance-validated outputs to the hospital governance subsystem. Routers or gateways may also perform limited AI inference and maintain a subset of the compliance ledger.

Security and Anomaly-Detection Subsystem

A hardware and software component of the hub responsible for monitoring access attempts, traffic patterns, and system logs to identify unauthorized access or anomalous traffic. Detection events generate corresponding compliance-ledger entries and may trigger alerts or protective responses.

Unauthorized Access

Any attempt to connect to, configure, or control the hub or its subsystems without valid governance-token authorization or credential authentication. Such attempts are immediately blocked by the governance subsystem and logged as security incidents.

Telehealth

Telehealth refers to the delivery, facilitation, or coordination of healthcare, monitoring, or patient-support services through digital or networked communication technologies that enable remote interaction between a patient, caregiver, or clinician. The term encompasses both synchronous and asynchronous exchanges, including but not limited to video or audio consultation, remote patient monitoring, clinical data transmission, prescription management, and communication of therapeutic, educational, or administrative content. Telehealth operations may be performed through the patient-facing subsystem, a tablet interface, or any connected communication platform linked via the hub or its associated gateway, with all activities recorded as compliance-controlled events within the governance framework.

Regulatory Oversight

Regulatory oversight refers to external or internal review mechanisms enabling auditing, certification, or supervisory access to compliance-ledger data or governance artifacts by authorized entities such as hospital administrators, regulators, or accreditation bodies, locally or across federated networks.

Patient

As used herein, the term patient is intended to encompass not only individuals receiving medical care but also any user, client, or monitored individual whose physiological, behavioral, contextual, or interactional data are observed, collected, processed, transmitted, or managed by the hub, by connected medical devices, or by any interoperable, networked, or federated subsystem capable of participating in the compliance-governed ecosystem. The patient may include a person situated within a healthcare facility, home-care environment, ambulatory setting, research site, or any monitored location in which data are generated or exchanged under medical, wellness, or safety-related supervision.

The term therefore includes, without limitation, clinical patients, outpatients, wellness users, residents of assisted-living or home-care facilities, remote-monitoring subjects, research participants, and other monitored or managed individuals whose data are validated, transmitted, or governed by the system or by connected institutional or third-party infrastructures, whether or not such monitoring occurs directly through the hub.

Monitored Individual

The term monitored individual refers to any person, user, client, subject, or participant whose physiological, behavioral, contextual, environmental, or interactional data are measured, acquired, processed, or transmitted by the hub, by any connected or interoperable subsystem, or by any third-party device or platform that interfaces with the compliance-governed ecosystem.

A monitored individual may include, without limitation, a hospital patient, outpatient, wellness user, caregiver, healthcare professional, or research participant whose activities, conditions, or interactions are captured or correlated within the system. The monitoring may occur continuously or intermittently, locally or remotely, and may be performed directly by the hub or indirectly through wearable devices, medical equipment, telehealth platforms, federated networks, or institutional infrastructures that interoperate with the compliance framework.

In certain embodiments, the term monitored individual is used interchangeably with patient, except where context distinguishes the monitored role from the clinical or therapeutic status of the individual, thereby encompassing all persons whose data contribute to or are managed within the compliance-ledger ecosystem.

Hub Hardware Architecture

The Hub (100) mandatorily includes a Power Management Subsystem (500) forming the electrical and network backbone of the device. Embedded within this subsystem is the AI-Ready Hub Hardware Interface Module (190), which constitutes the primary connector and ingress assembly for power and communication. The module accepts input from Power-over-Ethernet (POE), USB-C, or AC mains and distributes regulated energy through galvanically isolated circuits compliant with IEC 60601-1.

Beyond power delivery, the Hardware Interface Module (190) establishes an internal network backbone that propagates both electrical power and digital communication across all connected hub modules, including the Control Unit (700), PF-CSS (250), and AI Subsystem (340). This backbone enables synchronized power management and high-speed command exchange without external switches or adapters.

The module's authentication and state-change events are monitored and validated by the AI-Ready Hub Software Interface Module (795) operating within the Control Unit (700). All negotiation, fault detection, and source transitions (AC ↔PoE ↔USB-C) are logged through the Compliance and Governance Subsystem (600/780). As shown in FIGS. 1 and 2, the Hardware Interface Module (190) is a fixed connector element of the Power Management Subsystem (500) and not a detachable accessory.

Modular Receptor Assembly

Modular receptor assembly refers to the configurable mechanical, electrical, and data-interface structure of the hub designed to receive and secure interchangeable functional modules. Each receptor space provides standardized power and communication interfaces, enabling plug-and-play installation, replacement, or reconfiguration of modules without altering the chassis or disrupting powered operation.

In preferred embodiments, the modular receptor assembly comprises two or more standardized outlet spaces adapted to receive, individually or in combination:

- Standard electrical-outlet modules compliant with regional standards such as Schuko, NEMA, or successor formats;
- Medical-device integration modules providing sensor, data, or vendor-specific connectivity for clinical equipment;
- Nurse-call or functionally equivalent signaling modules enabling bedside or remote-alert activation; and
- Protective covers or blanking plates maintaining safety and ingress protection when slots are unused.

The modular receptor assembly is distinct from the AI-accelerator bay, which is a separate, dedicated module space configured to house high-performance computing hardware. Receptor-assembly dimensions and connector standards may vary by configuration-commonly available in two-slot and four-slot formats—to accommodate regulatory, architectural, or power-density requirements while maintaining forward compatibility with future module generations.

Artificial-Intelligence Execution Environment

Artificial-intelligence execution environment refers to the dedicated hardware and software domain within the hub configured to host, power, and operate one or more artificial-intelligence accelerator modules. The environment provides electrical, thermal, and data-interface resources that enable safe and compliant local model execution within the patient-care boundary.

The AI Receptor Slot (310) is physically positioned within the AI Inference Hardware Space (120) shown in FIG. 1 and FIG. 2, forming the primary interface between the AI Subsystem (340) and the Hub (100).

In preferred embodiments, the artificial-intelligence execution environment includes a dedicated bay dimensioned for accelerator hardware, equipped with integrated power connectors, high-speed network interfaces, and mechanical retention features ensuring secure installation and serviceability. It operates under supervision of the control unit and the compliance and governance subsystem, which together manage model loading, validation, data access control, and execution logging.

The environment supports local inference, analytics, and decision-support workloads, reducing reliance on external cloud services while maintaining compliance with institutional policies and regulatory constraints. Communication with external systems occurs through validated interfaces, and all inference outputs are recorded as compliance-controlled events in the ledger.

In certain embodiments, the artificial-intelligence execution environment may also include firmware or micro-orchestration layers enabling dynamic allocation of compute resources among AI models, energy-optimized operation, or secure shutdown in response to compliance or safety events.

In certain embodiments, the Artificial-Intelligence Execution Environment (AIEE) is configured not only for local inference execution but also for distributed or delegated inference across one or more remote nodes. The control unit may determine, based on policy, workload, or thermal conditions, whether an AI model should execute locally within the AIEE or be securely transmitted for execution to a remote institutional, cloud, or federated node. In all cases, the inference process remains under compliance governance, and results returned from remote execution are validated and ledgered identically to locally generated outputs. This design allows hybrid or adaptive AI deployment while maintaining traceability, auditability, and policy compliance across distributed environments.

Patient Association Mechanism

The hub includes a patient association mechanism configured to authenticate and personalize system behavior for an individual patient. Association may occur through a wearable bracelet, smartphone, badge, or equivalent token supporting cryptographic authentication.

Once association is verified, the hub activates personalized services such as telehealth, educational content, consent workflows, adherence tracking, secure payments, and optional entertainment. Credentials are automatically revoked or rotated upon discharge or reassignment, and every transaction is recorded in the compliance ledger with provenance data binding patient ID, hub identity, and policy version.

Patient Contextualization

In the context of this disclosure, the patient represents a generalized monitored user entity rather than a strictly medical subject. The term includes any person whose physiological, behavioral, or contextual information is collected, validated, or transmitted through the hub or its associated subsystems. This encompasses clinical patients in hospital settings, users in home-care or ambulatory environments, and clients of telehealth or wellness services.

The hub and its connected devices-including medical devices, wearable sensors, and patient-facing systems-treat all such monitored individuals uniformly under the governance and compliance framework. Credential management, identity association, and data-handling policies apply equivalently to all monitored users, regardless of clinical status or location.

Accordingly, when the specification or claims refer to a "patient," such reference shall be understood to include any user, client, or monitored individual whose interaction with the hub or associated medical devices generates compliance-controlled events, telemetry, or contextual metadata recorded in the ledger.

Power Subsystem

The power subsystem (110) constitutes the hub's primary energy distribution and safety-governed control domain. It is configured to deliver regulated, monitored, and logged electrical power to all connected modules and external devices, including medical-device integration modules, patient-facing systems, artificial-intelligence accelerators, and communication hardware.

The subsystem supports multiple present and future high-power-delivery standards, including but not limited to Power-over-Ethernet (POE, PoE++), USB-C Power Delivery, and any successor or functionally equivalent DC or hybrid power interface providing negotiated power management and intelligent fault protection. In certain embodiments, the subsystem also provides auxiliary ports for PoE or USB-C power outputs to peripheral medical or patient-facing equipment.

All electrical-safety and performance metrics, including voltage, current, temperature, and load distribution, are continuously measured and recorded in the compliance ledger under governance control. Deviations or abnormalities automatically generate compliance-controlled alerts and containment actions, ensuring both operational safety and regulatory traceability.

The subsystem may further provide power to other hub subsystems, including the control unit, artificial-intelligence execution environment, compliance and governance subsystem, and patient-facing information and services subsystem, as well as external patient or user devices such as bracelets, smartphones, and portable medical instruments.

Passive or active thermal-management mechanisms, including heat-dissipation channels, convection pathways, or temperature-responsive regulation, maintain energy and environmental stability across modules and the chassis.

When integrated within the compliance-validated execution environment, the power subsystem contributes to overall system assurance by correlating energy events, operational states, and device performance with governance policies, thereby forming a verifiable chain of electrical and procedural integrity across the hub and its connected ecosystem.

Control Unit (700)

The Control Unit (700) serves as the central orchestration processor of the Hub (100), integrating computing, communication, power-governance, and compliance functions within a unified management framework. It comprises at least one processor (710), volatile and non-volatile memory (720), and a non-transitory computer-readable storage medium (730) containing executable instructions that implement operational control, subsystem coordination, and governance-enforcement logic.

The Control Unit executes firmware and software components responsible for device discovery, data aggregation, validation coordination, and policy-driven resource management across all connected subsystems. These include, without limitation, the Power Management Subsystem (500)—which mandatorily contains the AI-Ready Hub Hardware Interface Module (190) forming the internal power and communication backbone—the Artificial-Intelligence Execution Environment (300), the Medical Device Integration Modules (220), and the Patient-Facing Information and Services Subsystem (250).

Residing within the Control Unit is the AI-Ready Hub Software Interface Module (795), which governs interoperability, discovery, and command routing between all subsystems. The Software Interface Module (795) supervises and communicates with the Hardware Interface Module (190) embedded in the Power Management Subsystem (500) to coordinate power-state transitions, network negotiation, and compliance telemetry.

Also embedded within the Control Unit is a Compliance and Governance Subsystem (780), implemented as a secure hardware-assisted software and firmware layer configured to enforce policy rules, manage ledger recording, and coordinate validation workflows. The Compliance and Governance Subsystem (780) corresponds functionally to the system-level Compliance and Governance Subsystem (600) illustrated in FIG. 6.

The Control Unit further incorporates secure communication interfaces, including the Identifier Display and Optical Scanning Window (790), Short-Range Wireless Interface Window (792) supporting Bluetooth®, NFC, or Wi-Fi pairing, and Long-Range Communication Interface (794) supporting hospital Wi-Fi, cellular, or satellite connectivity.

Integrated within the Control Unit (700) is the Communication Subsystem (800), which provides the physical and logical communication interfaces of the hub. The subsystem operates under the supervisory control of the Compliance and Governance Subsystem (780) and executes coordination tasks through the AI-Ready Hub Software Interface Module (795). This configuration ensures that all wired and wireless communications, including interfaces 790 through 794, are subject to governance validation before transmission or reception.

Through this integrated design, the Control Unit (700), working in concert with the AI-Ready Hub Software Interface Module (795) and the AI-Ready Hub Hardware Interface Module (190), functions as both an operational controller and a compliance-aware computing core. Together they ensure that all power, communication, and governance flows conform to institutional policies, regulatory standards, and safety requirements.

Compliance and Governance Subsystem (600/780)

The Compliance and Governance Subsystem (600) defines the policy-driven control domain that governs the integrity, accountability, and regulatory conformance of all Hub (100) operations. When instantiated within the Control Unit (700), it appears as Subsystem (780), performing the same functional role at the embedded level.

The subsystem includes a Validation Component (610) configured to verify operational events and data exchanges against compliance policies stored in the Policy Store (612). A Deny-by-Default Gate (614) enforces conservative policy execution by blocking any transaction or data release unless the prescribed validation criteria are satisfied.

Validated events generate Validation Ledger Entries (620), each of which is secured through Cryptographic Signing (630) to ensure authenticity, integrity, and non-repudiation. The signed entries are subsequently anchored (640) within a tamper-evident, distributed data structure-such as a blockchain, distributed ledger, or equivalent immutable framework-providing long-term traceability and auditability of all operational events.

An Audit and Compliance Feedback Loop (670) continuously monitors ledger records and operational telemetry for anomalies or deviations from policy. Upon detecting discrepancies, the subsystem issues corrective feedback to the Validation Component (610), achieving closed-loop assurance and adaptive policy correction.

The subsystem supports Federated Governance Network participation, synchronizing compliance data across institutional, regional, and cross-provider infrastructures to enable distributed validation, cross-site auditability, and longitudinal governance continuity.

Figure 6:
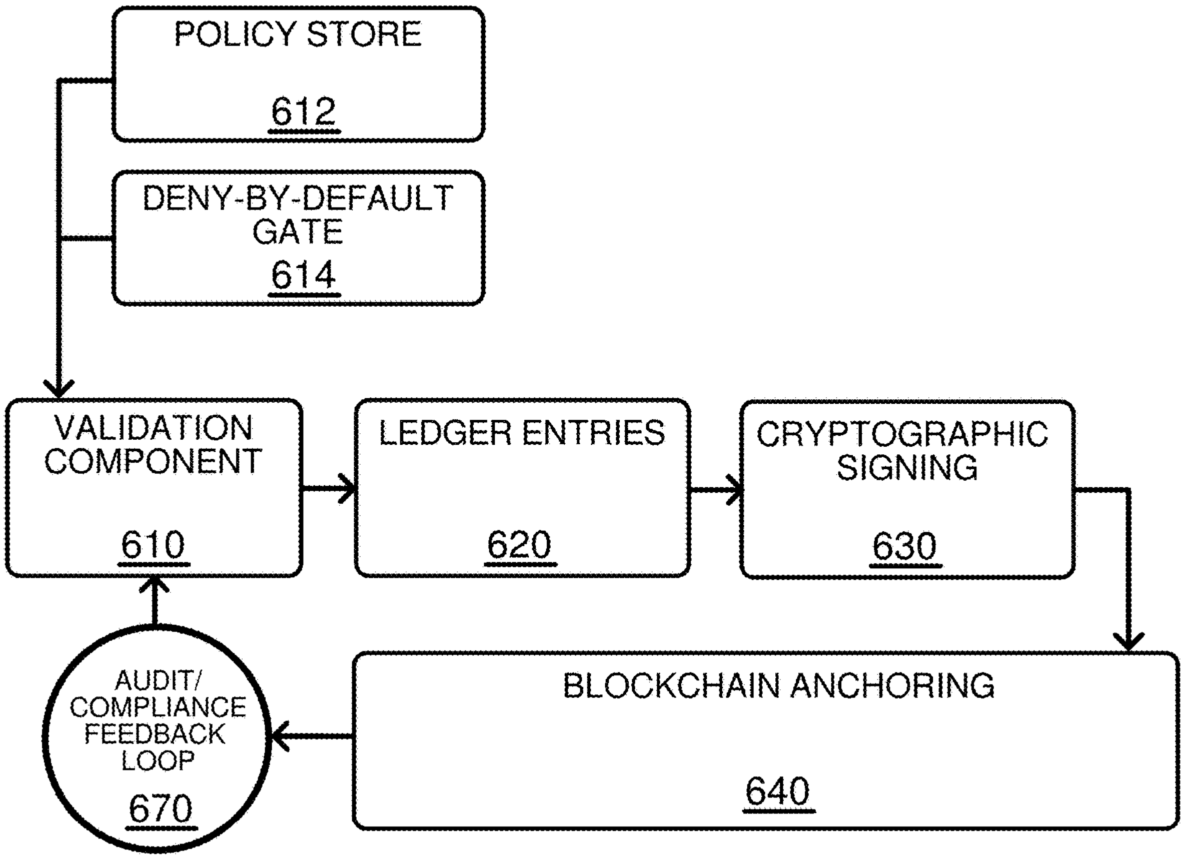
FIG. 6 depicts the Compliance and Governance Subsystem (600) and its logical workflow, including the Validation Component (610), Policy Store (612), Deny-by-Default Gate (614), Ledger Entries (620), Cryptographic Signing (630), Blockchain Anchoring (640), and Audit and Compliance Feedback Loop (670).

All recorded events—spanning power distribution, AI inference cycles, patient-credential operations, and device-configuration changes—are maintained within a compliance-validated execution environment, forming a verifiable record of operational trust, traceability, and regulatory alignment as illustrated in FIG. 6.

Communication and Networking

The Communication Subsystem (800) provides wired and wireless connectivity between the Hub (100), hospital infrastructure, and patient devices, coordinating data flow among the AI Subsystem (340), the Patient-Facing Information and Services Subsystem (PF-CSS 250), and the Medical Device Subsystem (740). It supports multiple physical and virtual transport layers, including wired Ethernet, Power-over-Ethernet (POE) through the AI-Ready Hub Hardware Interface Module (190), Wi-Fi, cellular (4G/5G), and optical interfaces, and can define private Wi-Fi or VLAN domains for each patient bed or clinical zone.

Operating within the Control Unit (700), the AI-Ready Hub Software Interface Module (795) manages all communication routing and discovery functions, serving as the middleware between subsystem (800) and the Hardware Interface Module (190). Through this relationship, the Software Interface Module (795) orchestrates both data and power-over-network operations, enabling secure backbone synchronization, link authentication, and adaptive bandwidth allocation while enforcing compliance and governance policies from subsystem (600/780).

Virtual Private Networks (VPNs) or zero-trust communication tunnels may be established for vendor servicing, remote diagnostics, or telemedicine access, each authenticated and logged by the Compliance and Governance Subsystem (600/780). When multiple hubs are deployed within a facility, the Communication Subsystem (800) can form a mesh-network topology in which each relay or forwarding event is transmitted through the Software Interface Module (795) and recorded as a compliance-controlled ledger entry.

The Logical Internal Network (850) extends the reach of the Communication Subsystem (800) beyond external connectivity, linking the Control Unit (700) to internal modules through secure, policy-controlled channels. This network carries both management and compliance traffic, allowing subsystem 800 to mediate between external hospital systems and internal hub components under the supervision of module 795.

Through the combined operation of modules (800), (795), and (190), the hub maintains an integrated, policy-governed network backbone that unifies electrical power distribution, communication control, and data integrity across all connected medical and patient-facing systems.

Patient-Facing Information and Services Subsystem (PF-CSS)

The Patient-Facing Information and Services Subsystem (PF-CSS 250) provides individualized, governance-controlled access to education, telehealth, consent management, adherence monitoring, secure payments, and optional entertainment services. The subsystem may be implemented as a software-defined service operating within the Hub (100), as a plug-in hardware module, or as an associated tablet interface securely paired with the Hub through the internal network backbone formed by the AI-Ready Hub Hardware Interface Module (190) and managed by the AI-Ready Hub Software Interface Module (795).

When embodied as a tablet or touch display, the PF-CSS functions as the primary user interface for patient interaction, providing authenticated access to context-aware information rendered by the AI Subsystem (340) and validated through the Compliance and Governance Subsystem (600/780). The tablet may communicate via the Hub's short-range wireless window (792) or through a secure docking connector linked to the Hardware Interface Module (190), allowing both power delivery and bidirectional data exchange over the same physical link.

All patient interactions are scoped to the authenticated patient identifier (410), and credentials are automatically revoked upon bracelet disassociation or patient discharge. Each patient-facing event-including access to clinical education materials, consent workflows, telehealth sessions, or entertainment-generates a compliance-controlled ledger entry recorded within subsystem (600/780) to ensure privacy, accountability, and regulatory traceability.

Through this integrated design, the PF-CSS (250) serves as the patient's secure digital access point to the Hub (100), bridging human interaction, AI-generated context, and institutional governance into a single, compliant interface.

Safety and Maintenance

To maintain operational safety, the hub incorporates both thermal management and predictive maintenance functions. Passive or active cooling elements ensure safe thermal limits under sustained AI and power workloads. Predictive maintenance routines continuously analyze subsystem metrics such as voltage drift, fan speed, temperature, and power load to forecast component degradation.

Anomalies or performance deviations are automatically logged in the compliance ledger and may trigger preventative alerts, maintenance scheduling, or module replacement requests, ensuring continuous compliance with hospital safety standards.

Illustrative/Narrative Example

Patient Association Example

In one embodiment, a patient admitted to a hospital room automatically associates with the hub through a wearable bracelet. After successful authentication and issuance of a governance token, the patient-facing subsystem activates personalized features such as telehealth consultations, consent management, adherence reminders, and secure payments.

All sessions are ledgered with provenance metadata binding patient ID, hub identity, and active policy version. Optional entertainment services operate under identical compliance control, maintaining strict privacy through automatic credential revocation upon discharge.

Mesh Networking Mode

In some embodiments, multiple hubs form an adaptive mesh network, allowing peer-to-peer relay of validated data packets. Each hop between nodes is cryptographically authenticated and logged in the compliance ledger. Mesh networking enhances resilience in environments where centralized network infrastructure is unavailable, ensuring continuity of regulated data exchange during outages.

In some embodiments, the AI-ready hub performs hybrid inference operations between local accelerator hardware and secure cloud infrastructure. Local models conduct preliminary inference and validation before transmitting encrypted feature sets to cloud services for advanced reasoning. Returned results are verified against compliance rules and appended to the ledger as provenance-bound events, maintaining full traceability of AI decision flow.

Governance-Controlled AR/VR Visualization

The hub interfaces with augmented- or virtual-reality devices to provide immersive visualization of validated patient data. All visualizations are authorized through governance tokens and cryptographically signed to prevent tampering. Each session produces a ledger entry containing session metadata, ensuring compliance and reproducibility.

Governance-Controlled Software Development Kit (SDK)

The system may provide a governance-controlled software development kit enabling third-party manufacturers or software vendors to create modular components for the hub.

All SDK access requires registration, digital certification, and issuance of a governance token defining permitted development scopes.

Each module compiled or deployed through the SDK is automatically scanned for security vulnerabilities, cryptographically signed, and recorded in the compliance ledger before activation.

This model supports an open specification for innovation while preserving compliance oversight and uniform auditability across all vendor contributions.

Training and Simulation Mode

The hub includes a simulation environment for staff training.

Training sessions use synthetic datasets derived from de-identified historical records.

All simulated operations are explicitly marked as non-clinical and stored in a segregated training ledger partition.

This ensures that educational exercises do not contaminate production compliance data while still demonstrating audit-ready governance functionality.

Mesh Networking Integration

In some embodiments, the AI-ready hub participates in a mesh-network topology enabling multi-hub data relay and fault-tolerant communication. Each hub within the mesh operates under governance control, forwarding only validated and signed packets. Relay transactions are logged as compliance-controlled events in the ledger, providing traceability of every data hop. The mesh configuration improves resilience against network disruptions and supports scalable deployment across large hospital campuses or distributed remote-care nodes.

Governance-Controlled AR/VR Visualization

The hub optionally interfaces with augmented-reality (AR) or virtual-reality (VR) systems to render validated medical information in immersive formats. Each AR/VR session requires issuance of a governance token and is cryptographically signed and recorded in the compliance ledger. This ensures that immersive displays are subject to the same audit controls as traditional data outputs.

Functional and Procedural or Structural Embodiment and Operational Modes

IV Pole Integration

In some embodiments, the AI-ready hub communicates with mobile IV poles equipped with infusion pumps, patient monitors, and physiological sensors. The IV-pole devices transmit validated data through the hub's medical-device integration modules.

The hub normalizes and validates this data, logs validation events in the compliance ledger, and forwards results to hospital information systems under governance control. Each IV-pole event is recorded as a compliance-controlled entry including provenance fields such as hub identity, patient identifier, module identifier, and policy version. This configuration ensures traceability, infusion-safety assurance, and continuous monitoring of patient vitals.

Smart IV Pole System

The Smart IV Pole System forms an integral component of the medical-device subsystem, extending conventional infusion infrastructure into an intelligent, compliance-governed data node within the patient-care boundary. Unlike traditional IV poles that serve purely as mechanical supports for infusion pumps and monitoring accessories, the Smart IV Pole incorporates embedded electronics, communication interfaces, and compliance-aware firmware designed to operate in concert with the hub (100).

In various embodiments, the Smart IV Pole System includes one or more data and power interfaces such as Power-over-Ethernet (POE, PoE++), USB-C, or other regulated DC connectors. These interfaces supply power to attached infusion pumps and sensors while enabling bidirectional data exchange with the hub. The pole may also host integrated sensors measuring infusion flow rate, pump status, or environmental parameters such as temperature and tilt angle, thereby supporting predictive maintenance and situational awareness.

The Smart IV Pole System may incorporate a communication subsystem configured for both wired and wireless operation, including short-range connectivity (BLE, UWB, RFID) for device pairing and long-range communication (Wi-Fi or cellular) for hospital network integration. Through these interfaces, the pole maintains a secure association with the patient via the patient association mechanism, linking physiological data streams to patient identity within the compliance ledger.

In certain embodiments, the pole further comprises an AI-assisted control unit configured to perform local data filtering, symbolic arbitration, or preliminary inference regarding infusion trends, alarm relevance, or patient state changes. Outputs from these functions are validated by the hub's compliance and governance subsystem (600) before any nurse-call or clinical-notification event is issued.

Each operational event—including device connection, infusion initiation, alarm state, and patient reassociation—is recorded as a compliance-controlled ledger entry. The Smart IV Pole System thus ensures that all infusion-related actions remain traceable, policy-constrained, and auditable under hospital governance standards.

Mechanically, the pole may include attachment rails and brackets for modular infusion pumps, power-supply adapters, and sensor accessories. When wall mounting is not feasible, the pole may operate as a standalone mobile unit powered by the hub or local supply, retaining full compliance connectivity and ledger synchronization upon reconnection.

In operation, the Smart IV Pole System acts as a distributed extension of the hub, merging the traditionally separate domains of bedside mechanical devices and digital compliance infrastructure. It thereby provides real-time clinical insight, automatic validation of therapeutic data, and seamless inclusion of infusion activities within the governance and audit ecosystem defined by the integrated hub platform.

Nurse Call and Telephony

The hub may integrate with existing nurse-call systems and VoIP telephony platforms. The patient may initiate assistance requests through a wearable bracelet, smartphone, or the PF-CSS interface.

As illustrated in FIG. 9, these communication and compliance interactions occur within the patient room configuration (900), integrating the Hub (100), PF-CSS (250), Compliance Subsystem (600), and associated medical devices.

Each request generates a compliance-ledger record identifying the patient, time, and handling response. The same framework supports telehealth video or audio communication under governance-token authorization, guaranteeing traceable interaction records for clinical accountability.

Vendor VPN Access

A vendor-specific VPN may be established through the communication subsystem to enable secure remote diagnostics, firmware updates, or log retrieval. Access is governed by compliance-token issuance and time-limited credentials.

All VPN sessions are logged with technician identity, session duration, and actions performed. Firmware packages are verified by cryptographic signature prior to installation, ensuring integrity and regulatory compliance.

Personal Area Network (PAN) Gateway

The hub may function as a personal area network gateway connecting local wearable sensors-such as heart-rate monitors, oxygen sensors, and mobility trackers—to the patient record.

Each data stream is normalized, validated, and logged as a compliance-controlled event. When connectivity is interrupted, buffered data remains within encrypted storage until synchronization resumes.

Private Wi-Fi Domains

Each patient room may include a private Wi-Fi domain provisioned by the hub, isolating infusion pumps, monitors, and patient tablets from general hospital networks.

These private domains enhance security, reduce interference, and enforce compliance isolation between patients. Credentials are dynamically generated under governance control and revoked at discharge.

Fallback Execution and Resynchronization

In some embodiments, the hub includes a fallback execution mode triggered upon loss of network connectivity. During this period, all validated data and compliance-ledger entries are cached locally within secure storage.

When network connectivity is restored, cached data and ledger entries are resynchronized with hospital information systems and governance networks, maintaining an unbroken audit trail.

Predictive Maintenance Framework

In some embodiments, the hub implements a predictive maintenance framework using machine-learning models trained on historical device metrics such as voltage, thermal variance, and signal integrity. These models identify early warning indicators for potential failures or calibration drift.

When a risk threshold is reached, the hub automatically generates a compliance-controlled alert recorded in the ledger and optionally notifies the hospital maintenance system or vendor network. This predictive framework reduces downtime and ensures continuous clinical readiness under regulatory oversight.

Post-Quantum Security Layer

The governance subsystem may employ post-quantum cryptographic primitives to future-proof communication and ledger integrity. Algorithms may include lattice-based or hash-based schemes validated through NIST standards.

All ledger transactions, token exchanges, and compliance attestations are signed using these primitives to ensure resistance to quantum decryption attacks.

Small Language Model Hosting

In some embodiments, the Artificial-Intelligence Execution Environment hosts one or more small language models optimized for multimodal reasoning at the bedside.

These models assist clinicians by translating medical-device outputs into human-readable summaries, generating compliance-validated alerts, or prioritizing nurse calls based on contextual relevance. The models operate under governance-token supervision to ensure safety and accountability.

Bracelet Charging and Credential Reset

The hub may include a charging dock for patient bracelets or identifiers. Upon discharge or reassignment, the bracelet's credentials are automatically revoked, and stored tokens are purged.

Charging events are recorded in the compliance ledger, and each reactivation requires issuance of a new governance token. This process ensures that only authorized patients can regain access after reassignment or maintenance.

Adaptive AI Alerting

The AI subsystem (340) may generate adaptive alerts by comparing real-time patient data against historical baselines. When a deviation exceeds statistically determined safety thresholds, an alert is issued through the nurse call system or PF-CSS.

Every adaptive alert, its justification, and its provenance are recorded in the compliance ledger. Alerts may also trigger corrective AI actions, such as pausing an infusion pump or notifying remote clinicians.

Role-Based Data Rendering

In some embodiments, the hub enforces role-based data rendering policies. For example, physicians may view high-resolution analytics, while nurses receive simplified visual indicators or alerts.

Rendering policies are enforced by the control unit and logged in the compliance ledger to maintain consistent governance.

Self-Diagnostics and Redundancy Verification

The hub executes self-diagnostic routines at scheduled intervals to confirm power subsystem health, communication bandwidth, and AI readiness.

Redundancy tests ensure backup systems such as UPS power or secondary networks are operational. All diagnostic outcomes are recorded in the compliance ledger for traceable certification of safety compliance.

Compliance Ledger Synchronization

In some embodiments, the AI-ready hub participates in distributed compliance-ledger synchronization across hospital sites. Ledger entries from each hub are cryptographically hashed and transmitted through secure channels to regional or institutional governance nodes. Synchronization ensures that audit events remain consistent across all participating sites while preserving local data sovereignty. Each synchronization cycle is validated against checksum records to prevent tampering or replay.

Credential Vault Management

The credential vault maintains transient credentials used by patients, clinicians, and subsystems. Upon issuance of a governance token, corresponding credentials are stored securely and associated with defined expiration intervals. When sessions terminate, the vault performs automatic revocation and purge, recording each operation as a compliance-controlled event. Vault contents may be mirrored to a remote governance node for disaster recovery under encrypted transmission.

Break-Glass Mode

Break-glass mode provides emergency access to critical clinical functions when standard authentication pathways are unavailable. Activation requires dual authorization by two distinct clinical actors or roles. The governance subsystem generates an immutable ledger entry containing justification, participant identifiers, and timestamps. When the emergency window closes, access rights revert to baseline policies, and an automatic compliance review is triggered.

Edge-Level Federated Learning

The hub supports federated learning across distributed nodes, allowing AI model training without transmitting raw patient data. Each hub computes encrypted gradient updates using local datasets. These updates are aggregated centrally to refine shared models while maintaining data privacy. Every contribution is signed, timestamped, and recorded in the compliance ledger for transparency and regulatory alignment.

Secure Timebase Validation

The system synchronizes its internal timebase through authenticated network-time (NTP), precision-time (PTP), or satellite (GNSS) signals. Every synchronization event is cryptographically validated to prevent spoofing. The verified timestamps serve as authoritative markers for all ledger entries, ensuring temporal integrity during regulatory audits.

Real-Time Location Service (RTLS) Integration

The hub integrates with real-time location services using Bluetooth Low Energy (BLE), ultra-wideband (UWB), or RFID protocols. RTLS data associates patient devices, caregivers, and assets with specific spatial coordinates. Each location update is validated under governance control and recorded as a compliance-controlled event, improving situational awareness and auditability.

Network Disruption Resilience

Upon detection of a network failure, the hub switches to autonomous offline mode. Validated data are cached locally, and all actions continue under the governance subsystem using previously issued tokens. When connectivity is restored, cached data are reconciled and merged with the distributed ledger, ensuring uninterrupted compliance continuity.

Adaptive Compliance Policies

The governance subsystem can dynamically update policy sets to reflect evolving clinical or regulatory mandates. When a new rule is issued, the subsystem retrieves signed policy bundles from an authorized governance node, verifies their signatures, and propagates them to active hubs. Each update is logged as a compliance-controlled event, including before-and-after hashes to enable audit comparison. The mechanism allows hospitals to remain compliant without firmware replacement or downtime.

Post-Quantum Security Layer

The governance subsystem may employ post-quantum cryptographic primitives to future-proof communication and ledger integrity. Algorithms may include lattice-based or hash-based schemes validated through NIST standards.

All ledger transactions, token exchanges, and compliance attestations are signed using these primitives to ensure resistance to quantum decryption attacks.

Software Bill of Materials (SBOM) Cataloging

The hub maintains an automatically generated software bill of materials enumerating all installed firmware, software components, and AI models.

Each component is hashed and versioned, with records stored in the compliance ledger for traceability. The SBOM can be exported for regulatory audits, ensuring transparency and cybersecurity accountability.

Predictive Network Optimization

The Communication Subsystem (800) may employ predictive analytics to anticipate bandwidth saturation, latency spikes, or failure probabilities. By leveraging locally trained AI models, the hub dynamically prioritizes packet routing and caching behaviors. These adaptive operations are recorded as governance-controlled events, linking every optimization decision to a compliance token and associated ledger entry.

Predictive Communication Recovery

Predictive communication logic monitors ongoing data exchanges and anticipates disruptions caused by network instability. Before loss occurs, the hub pre-caches critical patient and device data and establishes alternate routes through redundant channels or neighboring nodes. Upon re-establishment of stable connectivity, cached records are automatically reconciled and verified against the compliance ledger, preventing data loss or duplication.

Break-Glass Event Record

Every invocation of break-glass mode results in a structured event record containing clinician identity, event timing, and authorization metadata. The record is cryptographically anchored and stored in both local and federated ledgers, ensuring traceability and accountability during regulatory review or post-incident audit.

Predictive Maintenance and Diagnostics

The power and environmental control subsystems continuously monitor operating parameters such as temperature, electrical load, and fan speed. Predictive algorithms identify abnormal trends suggesting potential hardware failure. When thresholds are exceeded, maintenance alerts are generated and logged as compliance-controlled events. Corrective actions and component replacements are automatically linked to the originating alert record.

Quality-of-Service Prioritization

The control unit implements a dynamic quality-of-service (QoS) scheduler. Real-time clinical data streams receive highest priority, while non-critical tasks such as entertainment or software updates are deferred. The scheduler adapts automatically based on network load and patient acuity, maintaining operational safety and compliance. Each QoS change is recorded in the ledger for traceability.

AI Explainability Manifest

Each AI model deployed within the hub includes an explainability manifest containing dataset lineage, performance metrics, and validation identifiers. Manifests are attached to inference results and stored alongside ledger entries, providing regulators and clinicians transparent visibility into AI decision pathways.

Secure Firmware Update and Attestation

Firmware images for subsystems are distributed as signed update packages. Before installation, the hub verifies digital signatures using the governance key hierarchy and records validation results in the ledger. After successful update, the system issues an attestation event to the governance node, certifying that the new firmware matches its registered checksum. Any failed verification automatically triggers quarantine of the update package and an alert to compliance officers.

Multilingual Interface Management

The patient-facing subsystem supports multilingual rendering of all interactive content. Language translation and contextual adaptation are handled by AI components operating under governance control. Each translation output is recorded in the compliance ledger with provenance fields identifying model version, policy, and operator.

Session Termination and Credential Revocation

Upon patient discharge, room reassignment, or bracelet disassociation, the governance subsystem initiates session termination. All active patient-facing sessions are closed, credentials revoked, and cached data anonymized or purged. A compliance-ledger entry documents each termination, including provenance fields such as hub identity, patient identifier, and policy version, ensuring complete accountability.

Data Validation and Provenance Recording

Every transaction processed by the hub, whether device output, AI inference, or patient interaction, undergoes multilayer validation before release. Validation steps include syntactic checking, schema compliance, encryption verification, and rule-based conformance against hospital policies. Once confirmed, the event is encapsulated with a provenance record containing device identity, policy version, timestamp, and hash chain position, and stored in the compliance ledger. This assures regulators that every transmitted datum can be traced back to its origin and authorization context.

Hardware Security Module (HSM) Anchoring

Sensitive cryptographic operations, including token generation and ledger signing, are performed inside a hardware security module embedded within the hub. The HSM enforces secure key storage, random number generation, and cryptographic isolation from the main processor. Each HSM invocation is recorded in the ledger with provenance metadata. When federated governance nodes validate ledger entries, the HSM's attestation proofs confirm hardware authenticity and operational integrity.

Device Interoperability Gateway

The hub includes a gateway interface that translates data from heterogeneous medical devices using standard formats such as HL7, FHIR, and IEEE 11073. The gateway normalizes incoming streams, detects inconsistencies, and annotates each data element with device metadata and validation status. All translation and normalization operations are logged under governance control, ensuring consistent interoperability without manual configuration.

Clinical Workflow Automation

The AI subsystem (340) supports automated workflow triggers such as medication verification, infusion monitoring, and consent tracking. When an AI model detects completion of a required step or violation of a protocol, it notifies the nurse-call or alert subsystem. The governance token associated with that workflow item ensures that automation decisions remain auditable. Each trigger or intervention is preserved in the ledger as a compliance event.

Thermal and Environmental Safety

Temperature sensors embedded within the chassis continuously measure internal heat distribution. The control unit compares readings to a calibrated safety profile. If anomalies are detected, fan speed or power output is adjusted automatically. Excessive deviation generates a compliance event and optional maintenance ticket. All environmental safety actions are stored in the ledger for inspection by biomedical engineers.

Remote Governance Console

Administrators may manage multiple hubs through a secure remote governance console. The console provides real-time dashboards for ledger synchronization status, device health, and compliance alerts. Access to the console requires multi-factor authentication and issuance of a governance token. Each console action—configuration change, policy approval, or report generation—is logged as a compliance-controlled event to prevent unauthorized modification of governance state.

Integration with Hospital Information Systems

The control unit maintains bidirectional interfaces with electronic medical record (EMR) and laboratory information systems (LIS). Validated data packets from the hub are exported using hospital-approved APIs or messaging standards. Conversely, the EMR may push context updates such as patient admission or discharge events back to the hub. All transactions between systems are logged in both environments, maintaining synchronized provenance trails.

Compliance-Controlled Telemetry Export

The hub can export selected telemetry metrics—temperature, power, AI-inference latency, or device error rates—to external monitoring systems. Before export, data are filtered and anonymized under policy control. A governance token is required for each export stream, and an immutable ledger entry documents recipient identity, purpose, and authorization scope. This prevents uncontrolled data sharing while enabling legitimate system oversight.

Multi-Tenant Isolation

In shared infrastructure environments, such as research hospitals or integrated networks, multiple departments may host independent virtual hubs within the same hardware. Each tenant maintains its own governance token domain and logically separated ledger partition. Cross-tenant data exchange is prohibited unless an explicit inter-tenant policy is approved and logged. This architecture prevents privilege escalation and data leakage between institutional divisions.

Energy Management and Sustainability

The power subsystem implements adaptive energy management algorithms that modulate power delivery and cooling based on device load, time of day, and hospital energy-saving policies. Energy-usage metrics are recorded in the ledger to support sustainability reporting and compliance with green-procurement standards. Any deviation from safe operating thresholds automatically triggers protective shutdown and audit notification.

Role-Based Access Control (RBAC)

Every user, subsystem, or API call operates under a defined role with limited privileges. The governance subsystem enforces least-privilege principles through token scoping. Role assignments are stored in encrypted form within the credential vault. Changes to RBAC configuration-additions, removals, or privilege escalations-require multi-factor authorization and are permanently logged in the ledger.

Audit Trail Visualization

Compliance officers may view real-time or historical audit trails through a visualization interface integrated with the governance console. Ledger entries can be filtered by date, device, clinician, or policy rule. The visualization component itself is compliance-controlled; all queries and exports generate meta-entries referencing the audit view. This enables regulators to verify not only the data but also the viewing process.

Secure Backup and Disaster Recovery

The hub supports automatic, encrypted backup of configuration and compliance data to redundant storage systems. Backup operations occur at configurable intervals under governance token authorization. During restoration, the system verifies digital signatures and hash integrity before re-activation. All backup and restore operations are logged, allowing auditors to reconstruct recovery history in the event of incident review.

Device Certification and Provenance Registry

Each medical device integrated into the hub possesses a certification record issued by its manufacturer or regulatory authority. The hub maintains a provenance registry mapping device identifiers to certification hashes and expiration dates. Upon device connection, the hub cross-checks the record before accepting data. Uncertified or expired devices are quarantined automatically, and rejection events are ledgered.

AI Model Version Control

All AI models deployed within the hub are version-controlled. Each model has a unique identifier, checksum, training-data reference, and validation metric set. Model deployment, rollback, or deprecation is performed only under governance token authorization. Every modification produces a ledger entry linking prior and new versions, providing a full lineage for regulatory transparency.

End-of-Life Decommissioning

When a hub or subsystem reaches end-of-life, the governance subsystem performs controlled decommissioning. Stored credentials, policy keys, and ledger fragments are securely wiped or cryptographically retired. A decommission certificate containing the final hash state and attestation signatures is issued to the hospital's compliance archive. This ensures the hardware and its digital history are conclusively retired under verifiable audit conditions.

Module Certification and Signing Process

Third-party modules must pass automated and manual certification steps before acceptance into the operational ecosystem.

Each certification step generates a compliance record identifying developer, code hash, test version, and approval officer.

Upon approval, the governance subsystem signs the module with a digital certificate referencing its compliance lineage.

Any subsequent modification or patch invalidates the signature and triggers recertification.

Third-Party Manufacturer Integration Framework

The hub supports integration of external manufacturers that produce hardware attachments or functional extensions conforming to published electrical and communication specifications.

Each manufacturer must register its product through the governance network and receive a unique hardware identifier.

When connected, the hub verifies the manufacturer signature and checks conformance metadata before activation.

Integration events and verification outcomes are permanently logged in the ledger.

Device Discovery and Authentication

When a new peripheral is physically connected or wirelessly paired, the hub initiates device discovery by querying embedded certificates.

Authentication is achieved using asymmetric cryptography verified through the governance subsystem.

Once authenticated, the device is assigned to an operational domain, and an onboarding ledger entry is created.

Unverified or non-compliant devices are automatically quarantined until administrative action is taken.

Plug-and-Play Compliance Negotiation

Following successful authentication, the hub and device exchange compliance profiles.

These profiles enumerate supported encryption standards, firmware versions, and operational constraints.

If the profiles differ, the governance subsystem mediates to establish the highest mutually compliant mode of operation.

The final negotiated configuration is recorded in the ledger, ensuring traceable conformity across diverse hardware.

Adaptive Firmware Containerization

Firmware for modular devices is deployed in signed containers managed by the governance subsystem.

Each container isolates the firmware runtime, preventing direct access to system resources.

When firmware updates occur, old versions remain archived until the new build passes validation tests.

This structure ensures backward traceability, rapid rollback capability, and secure update provenance.

Safety-Critical Process Isolation

Safety-critical functions such as infusion pump control, patient identification, and AI inference validation operate in isolated execution domains.

Inter-process communication between domains is restricted through secure message queues authorized by governance tokens.

If a process attempts to cross boundaries without authorization, the action is blocked and reported as a compliance alert.

Isolation guarantees that safety processes remain verifiable and unaffected by ancillary software activity.

Intrusion Detection and Response System

An embedded intrusion-detection engine monitors network traffic, file integrity, and system calls for malicious patterns.

When anomalies exceed predefined thresholds, the system initiates an automated response, including token revocation, user lockdown, and forensic snapshot generation.

All incidents, regardless of severity, are recorded in the compliance ledger with cryptographic proof of detection time and system state.

Cryptographic Health Monitoring

The hub continuously monitors cryptographic subsystems such as key lifetimes, signature validity, and entropy generation.

When a cryptographic component nears expiration or anomaly, the governance subsystem generates proactive renewal requests.

Any cryptographic failure triggers an automatic switch to safe mode, halting all data transmission until the issue is resolved and logged as a compliance event.

Secure Communication Channels

All communication paths—wired or wireless—are encapsulated within secure tunnels utilizing mutual authentication.

Keys are negotiated under the governance token framework and rotated at defined intervals.

Traffic is inspected for policy compliance and encrypted end-to-end, with session metadata retained in the ledger to verify confidentiality and integrity post-operation.

Event Stream Compression and Retention Policy

To optimize storage while maintaining audit completeness, the governance subsystem employs compression algorithms on historical ledger data.

Each compressed segment includes a Merkle-tree root enabling full reconstruction if needed.

Retention policies are configurable under regulation, ensuring that essential compliance evidence remains accessible within statutory timeframes.

Continuous Compliance Testing Environment (CCTE)

The system includes a self-testing environment that periodically executes simulated clinical and data-handling operations.

Results are compared against compliance baselines, and deviations automatically generate alerts.

The entire test suite, its outcomes, and remediation steps are logged in the ledger to demonstrate ongoing conformity to safety and regulatory standards.

Multimodal Sensor Fusion Interface

The hub supports simultaneous ingestion of diverse sensor modalities-visual, acoustic, and biometric.

The AI subsystem (340) fuses these inputs to derive composite clinical indicators such as distress or fall detection.

Fusion operations are tagged with sensor provenance metadata and associated AI model identifiers, maintaining a transparent inference chain.

Patient-Centric Feedback Loop

Patients can provide immediate feedback through the PF-CSS on device comfort, interface usability, or perceived care quality.

Feedback entries are processed under governance control, anonymized, and appended to a quality-assurance ledger.

These records inform future regulatory updates and manufacturer improvements, forming a continuous improvement cycle.

Secure Cloud Telemetry Bridge

The Communication Subsystem (800) may establish a telemetry bridge to secure cloud services for aggregated analytics.

All transmitted data are encrypted, pseudonymized, and validated against compliance filters before departure.

The bridge maintains synchronized counters to ensure no unverified transmissions occur.

Every upload and acknowledgment is mirrored in the local ledger.

Governance-Controlled De-Identification Engine

A de-identification engine processes personal identifiers before data export or external processing.

Using policy-defined rulesets, the engine removes or obfuscates patient identifiers while preserving referential linkage for authorized re-identification.

Each de-identification action is token-scoped and recorded in the ledger to ensure irreversible accountability.

Adaptive Policy Enforcement Learning

AI models monitor operational compliance performance, detecting repetitive human or system errors.

The governance subsystem uses these observations to propose policy adjustments or workflow modifications.

Suggested adjustments are reviewed and approved by compliance officers before activation.

All training cycles and resulting policy evolutions are recorded for longitudinal traceability.

Intelligent Power-Off and Recovery Logic

Before any intentional shutdown, the control unit performs safe-state transitions, closing patient sessions, flushing caches, and finalizing ledger entries.

Upon restart, the system verifies ledger continuity and integrity before re-enabling operations.

If discrepancies are found, the hub enters diagnostic mode and generates a non-compliance event requiring administrative resolution.

This procedure ensures that no compliance gap or data loss occurs during power-cycle transitions.

Predictive Communication Management

The hub incorporates predictive communication algorithms capable of anticipating link degradation, congestion, or device latency. Upon prediction of such events, the hub automatically reroutes or caches validated data to maintain continuous service. Predictive decisions and cache activations are logged as compliance-controlled events, ensuring that all network optimizations remain transparent and auditable under governance supervision.

Edge-Level Federated Learning

In some embodiments, the local AI subsystem (340) participates in federated-learning networks where encrypted model updates are exchanged between hubs and a central aggregator. No raw patient data is shared. Each model-update transaction is recorded in the compliance ledger with provenance fields including hub identity, policy version, and model checksum, thereby enabling collaborative training while preserving privacy and compliance.

Break-Glass Mode and Event Logging

The hub provides an emergency override mode known as "break-glass." When activated by authorized clinicians, standard authentication requirements are temporarily bypassed to permit immediate clinical intervention. Activation requires dual confirmation, operates for a limited time window, and automatically generates a break-glass event record in the compliance ledger identifying participants, timestamps, and justification. Upon termination, all privileges are revoked and normal governance enforcement resumes.

In some embodiments, AI workloads are distributed between local accelerator modules and remote cloud inference services. Outputs from both environments are cryptographically validated and cross-recorded in the compliance ledger to ensure that clinical or operational decisions derived from hybrid inference maintain full governance traceability and parity of authorization.

AI Explainability Manifest Integration

Each AI model hosted in the hub includes an embedded explainability manifest describing dataset lineage, validation metrics, and model-version identifiers. When an inference is performed, the manifest is attached to the output and logged in the compliance ledger. This ensures transparency, accountability, and the ability for regulators or clinicians to trace AI decisions back to validated training sources.

Predictive Maintenance and Lifecycle Monitoring

Beyond real-time operation, the hub continuously analyzes subsystem telemetry to predict maintenance needs and component replacement cycles. Deviations in temperature, voltage, or compute load generate predictive-maintenance alerts recorded in the compliance ledger. This proactive monitoring reduces downtime and ensures ongoing compliance with medical-device safety standards.

Extended Definition

Compliance Ledger Variants

The compliance ledger may be instantiated in several forms, including a local cryptographically signed database, a distributed ledger system, or a hybrid model combining both.

In each case, immutability and provenance are preserved through cryptographic signatures and anchored timestamps. Ledger data structures are optimized for role-based queries, enabling auditors to trace any event without revealing patient-identifying data.

Federated Hub Networks Across Hospitals

Multiple AI-ready hubs may operate in a federated network across hospitals or care facilities. Each hub maintains its own compliance ledger while synchronizing selected entries with a centralized governance service.

This federated arrangement enables cross-site policy harmonization, global auditing, and distributed learning while maintaining data privacy and local autonomy.

Federated Governance Network

The term "federated governance network" refers to a distributed or semi-distributed compliance and data-coordination framework in which multiple hubs, systems, or nodes-whether located within a single healthcare institution, across multiple institutions, or spanning regional or cross-provider infrastructures-exchange or synchronize compliance-controlled data, policies, or governance tokens under authenticated and verifiable rules.

In certain embodiments, the network may include local governance domains within a single hospital or institutional environment, configured to synchronize ledger entries and policy versions among internal hubs; cross-provider infrastructures enabling interoperability and compliance-sharing among independent hospitals, clinics, or home-care facilities; and regional or national governance networks enabling oversight by regulatory bodies, insurers, or accreditation entities.

Each node within the network may maintain a full or partial copy of the compliance ledger and share cryptographically signed updates representing validated events. This structure supports distributed validation, cross-site auditability, longitudinal compliance assurance, and policy harmonization, enabling coordinated audits and governance updates without centralizing identifiable patient data.

Participation in the federated governance network may occur actively or passively, including systems capable of federation through standardized interfaces, distributed ledgers, or policy synchronization frameworks, regardless of whether such federation is currently enabled or connected.

The federated model further provides resilience against single-point failures, preserves chain-of-custody for compliance validation, and ensures that governance and compliance rules are consistently applied across connected or connectable nodes.

Hybrid Federated-Cloud Governance

In advanced deployments, governance nodes operate in hybrid topologies spanning on-premise servers and regulatory-approved cloud environments. Synchronization of compliance records occurs through secure channels with dual attestation. This approach enables scalability while preserving audit parity between cloud and hospital environments.

Cross-System Policy Federation

The governance subsystem supports federation with external compliance platforms such as regional regulators or accreditation bodies. Policy documents and attestation proofs can be exchanged using standardized schemas. Each exchange is cryptographically signed and appended to the ledger. This mechanism creates an inter-organizational trust chain, reducing redundant audits and ensuring global traceability of compliance artifacts.

Cryptographic Provenance Linking

Ledger entries reference one another using chained hash pointers, forming a tamper-evident sequence. When multiple ledgers exist across federated nodes, cross-hash anchors are periodically inserted, binding the timelines together. This technique provides mathematical assurance that historical records have not been altered, even across institutions or jurisdictions.

Open Specification Dissemination

Hospitals and vendors may access a controlled repository of interface specifications describing connector dimensions, data-exchange protocols, and safety tolerances.

The repository is hosted under governance control; all downloads and acknowledgments are ledgered.

This openness promotes innovation in peripheral design while ensuring that all third-party products operate within certified safety and compliance boundaries.

Federated Governance Network Synchronization

Multiple hospitals or remote-care organizations may deploy hubs that participate in a federated governance network. Compliance ledgers are synchronized via cryptographically signed updates that maintain patient anonymity while ensuring consistent enforcement of policy rules across institutions. This arrangement supports regional or national audit frameworks without centralizing sensitive patient data.

Bracelet (410)

A patient-specific wearable identifier device configured for continuous or intermittent wireless communication with the Hub (100) through one or more short-range protocols including Bluetooth Low Energy (BLE), Near-Field Communication (NFC), or Radio-Frequency Identification (RFID). The bracelet stores a cryptographically secured patient identifier and serves as the primary token for authentication, association, and credential activation within the patient-care boundary. When docked in the Bracelet Dock (910), it recharges and resets credentials under governance control. All bracelet association, disassociation, and charging events are recorded as compliance-controlled entries in the ledger.

Bracelet Dock (910)

A charging and data-reset station for the patient identification bracelet (410). It performs both energy replenishment and credential reinitialization under the governance control of the Compliance Subsystem (600).

Communication Subsystem (800)

Figure 8:
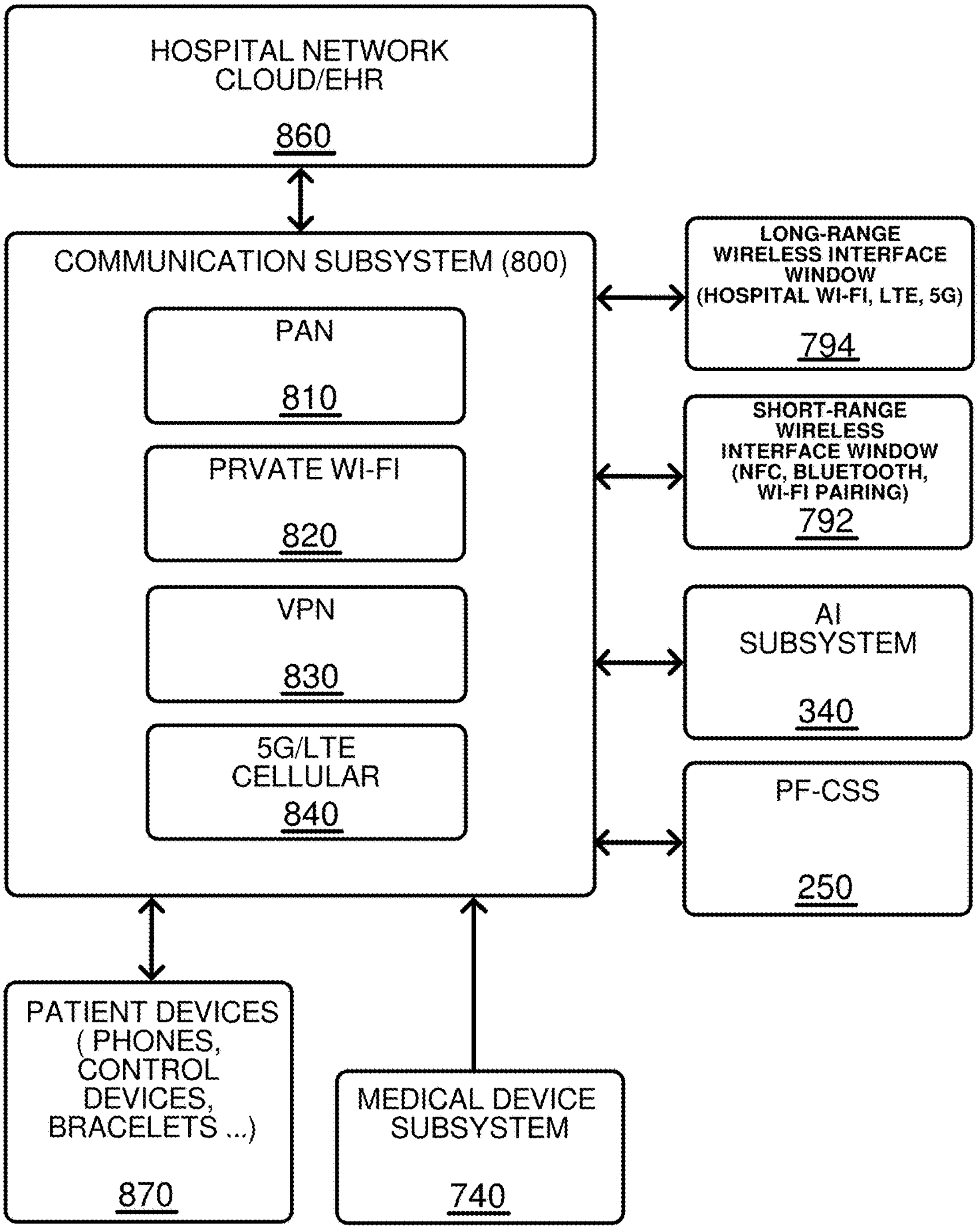
FIG. 8 shows the Communication Subsystem (800) and its layered connectivity, comprising the Personal Area Network (PAN 810), Private Wi-Fi Network (820), Virtual Private Network (VPN 830), and 5G/LTE Cellular Interface (840). The subsystem interfaces with the AI Subsystem (340), PF-CSS (250), Medical Device Subsystem (740), Patient Devices (870), and external Hospital Network or Cloud/EHR Infrastructure (860).

A hardware-and-software networking framework providing wired and wireless connectivity between the Hub (100), institutional hospital networks, and patient-facing devices. The subsystem encompasses Personal Area Network (PAN 810), Private Wi-Fi Domain (820), Virtual Private Network (VPN 830), and long-range cellular or optical interfaces (840). It authenticates and encrypts all transmissions under governance-token control, routes validated data between the AI Subsystem (340), PF-CSS (250), and Medical Device Subsystem (740), and records each transmission as a compliance-controlled ledger entry. The subsystem ensures redundancy, policy-constrained routing, and secure integration with external Electronic Health Record (EHR) or cloud infrastructures as illustrated in FIG. 8.

PAN (810)

A Personal Area Network interface providing short-range connectivity to nearby medical and patient devices within the proximity of the Hub (100), facilitating secure data exchange with bracelets, smartphones, or control peripherals.

Private Wi-Fi Domain (820)

A secure wireless network channel dedicated to hospital or room-level communications, operating under VPN (830) or local routing rules to maintain segregation between patient and institutional traffic.

Patient

As used herein, the term patient is intended to encompass not only individuals receiving medical diagnosis, treatment, or observation but also any user, client, subject, or monitored individual whose physiological, behavioral, contextual, or environmental data are observed, collected, processed, transmitted, or governed by the hub, by one or more connected medical devices, or by any interoperable, networked, or federated subsystem participating in the compliance-governed ecosystem.

The term extends beyond conventional hospital inpatients to include persons situated in home-care, ambulatory, wellness, rehabilitation, assisted-living, telehealth, research, or institutional environments, where data are generated, validated, or transmitted under medical, safety, or regulatory supervision.

In exemplary embodiments, a patient may include, without limitation:

- A hospitalized individual connected to infusion pumps, monitors, or other medical devices interfaced through the hub;
- A home-care recipient monitored via wearable sensors, tablets, or connected smart IV pole systems;

- A wellness user or research participant providing physiological or behavioral data through personal devices or federated telehealth platforms;
- A remote individual participating in a teleconsultation, whose biometric or contextual data are transmitted to a hospital or governance network; or
- A resident of a long-term care facility whose devices synchronize data with a federated governance or compliance-ledger system.

The term patient therefore includes any individual whose data are monitored, managed, or validated by the system, regardless of whether the monitoring occurs directly through the hub or indirectly through interoperable devices, federated infrastructures, or third-party systems that exchange compliance-governed information.

The embodiments described herein collectively define an extensible architecture for compliance-controlled medical infrastructure. The AI-ready hub functions as a foundational platform that integrates medical devices, local and distributed intelligence, patient interfaces, and cryptographic governance. Variations and successor technologies may be implemented without departing from the scope of the invention, provided that compliance logging, provenance tracking, and governance enforcement remain integral to system operation.

Referring now to FIG. 1, the illustration depicts representative embodiments of the AI-Ready Hub (100) and its structural variations. The hub is shown as a modular, wall-mounted or surface-mounted clinical hardware assembly configured for regulated healthcare environments. The figure presents both in-wall and on-wall configurations (170 through 182) and a multiple-configuration view (150) demonstrating interchangeability of functional modules within a standardized chassis.

At the upper portion of the hub, a Power Supply Block (110) and an integrated AI-Ready Hub Hardware Interface Module (190) are illustrated. These elements together form the electrical and network ingress for the system, providing regulated power and communication coupling through Power-over-Ethernet (POE), USB-C, or AC mains inputs. The Hardware Interface Module (190) is a fixed component of the mandatory Power Management Subsystem (500) and establishes the internal power-and-data backbone of the hub.

Beneath the power section resides the Control Unit (700), which houses the AI-Ready Hub Software Interface Module (795) and the Compliance and Governance Subsystem (780). The Control Unit (700) performs orchestration, authentication, and compliance-governed communication across all connected subsystems. It interfaces upward to the power subsystem (500) through module (190) and downward to the Patient-Facing Information and Services Subsystem (PF-CSS 250) and the Modular Receptor Assembly (200). Within this hierarchy, the Control Unit (700) manages AI workloads executed in the Artificial-Intelligence Execution Environment (300) and coordinates data routing through the Communication Subsystem (800) under oversight of subsystem (780).

The PF-CSS (250) is depicted both as an integral front-panel module and as an optional tablet interface that may dock or wirelessly associate with the hub through the backbone established by modules (190) and (795). The Modular Receptor Assembly (200) accepts Medical Device Integration Modules (220), allowing attachment of clinically approved devices without additional adapters. Standardized Power Plugs (210) and Protective Covers (230) are provided for safety and service access.

Each physical variant—in-wall mounted hub (170), in-wall mounted hub populated with modules (172), on-wall mounted hub (180), and on-wall mounted hub populated with modules (182)—shares the same functional architecture and compliance-governed backbone. A Wall-Mounted Back Component (160) secures the chassis to structural framing while preserving airflow and service clearance.

Collectively, the elements shown in FIG. 1 illustrate that the AI-Ready Hub (100) integrates mechanical, electrical, and computational domains into a single governance-controlled platform. The Power Supply Block (110) and Hardware Interface Module (190) provide safe, isolated power ingress; the Control Unit (700) and Software Interface Module (795) deliver operational intelligence and policy enforcement; and the PF-CSS (250) and Modular Receptor Assembly (200) enable patient interaction and medical-device connectivity. Together they form a modular yet unified infrastructure capable of local AI inference, secure communication, and compliance-verified operation within the clinical environment.

Referring now to FIG. 2, the drawing illustrates an exploded view of the AI-Ready Hub (100) showing the relative positioning and interconnection of its primary subsystems and modular assemblies. The figure demonstrates how electrical, computational, and patient-interface components integrate within a unified chassis to create a compliance-governed, AI-enabled medical-grade platform.

At the uppermost region, a Power Supply Block (110) and an embedded AI-Ready Hub Hardware Interface Module (190) are depicted. These elements together constitute the ingress and distribution layer of the hub's mandatory Power Management Subsystem (500). The Hardware Interface Module (190) provides standardized electrical coupling and network ingress through Power-over-Ethernet (POE), USB-C, or AC mains inputs. It contains isolation circuitry compliant with IEC 60601-1 and establishes the physical backbone that simultaneously distributes regulated power and internal communication throughout the system.

Immediately below the power section is an AI Inference Hardware Space (120) that accommodates processors, accelerators, or other devices forming the Artificial-Intelligence Execution Environment (300). This space interfaces directly with the Control Unit (700), enabling local inference, data aggregation, and policy-driven coordination of AI workloads. The Control Unit (700) houses the AI-Ready Hub Software Interface Module (795) and the Compliance and Governance Subsystem (780), which together manage authentication, encryption, and event validation across all operational pathways. Through secure protocol exchanges, module (795) supervises module (190) for power-state negotiation, network synchronization, and compliance telemetry.

Positioned beneath the Control Unit (700) is the Patient-Facing Information and Services Subsystem (PF-CSS 250). In the embodiment shown, the PF-CSS is implemented as a detachable front-panel module that may also function as an associated tablet interface. It provides the primary patient interaction surface, offering telehealth, consent, and educational services rendered by the AI Subsystem (300) and verified through the Compliance Subsystem (600/780). The PF-CSS connects through the internal backbone governed by modules (190) and (795), enabling both data exchange and power delivery over a single secure link.

Below the PF-CSS (250) resides the Modular Receptor Assembly (200), which receives and secures Medical Device Integration Modules (220). These modules provide standardized connection points for peripheral medical devices, sensors, and hospital systems. The lower section of the hub further includes Standard Power Plugs (210) for auxiliary or legacy equipment and Protective Covers (230) to maintain ingress protection and patient safety when modules are not installed.

The exploded arrangement shown in FIG. 2 demonstrates the hierarchical architecture of the AI-Ready Hub (100): power and network ingress via the Hardware Interface Module (190); computation and governance through the Control Unit (700); patient interaction and device integration via subsystems (250) and (220); and safety assurance through standardized electrical interfaces (210) and (230). All components interconnect through the Logical Internal Network (850) managed by the Software Interface Module (795) under supervision of the Compliance and Governance Subsystem (780), providing a unified, auditable, and regulation-compliant operating environment for clinical deployment.

Figure 3:
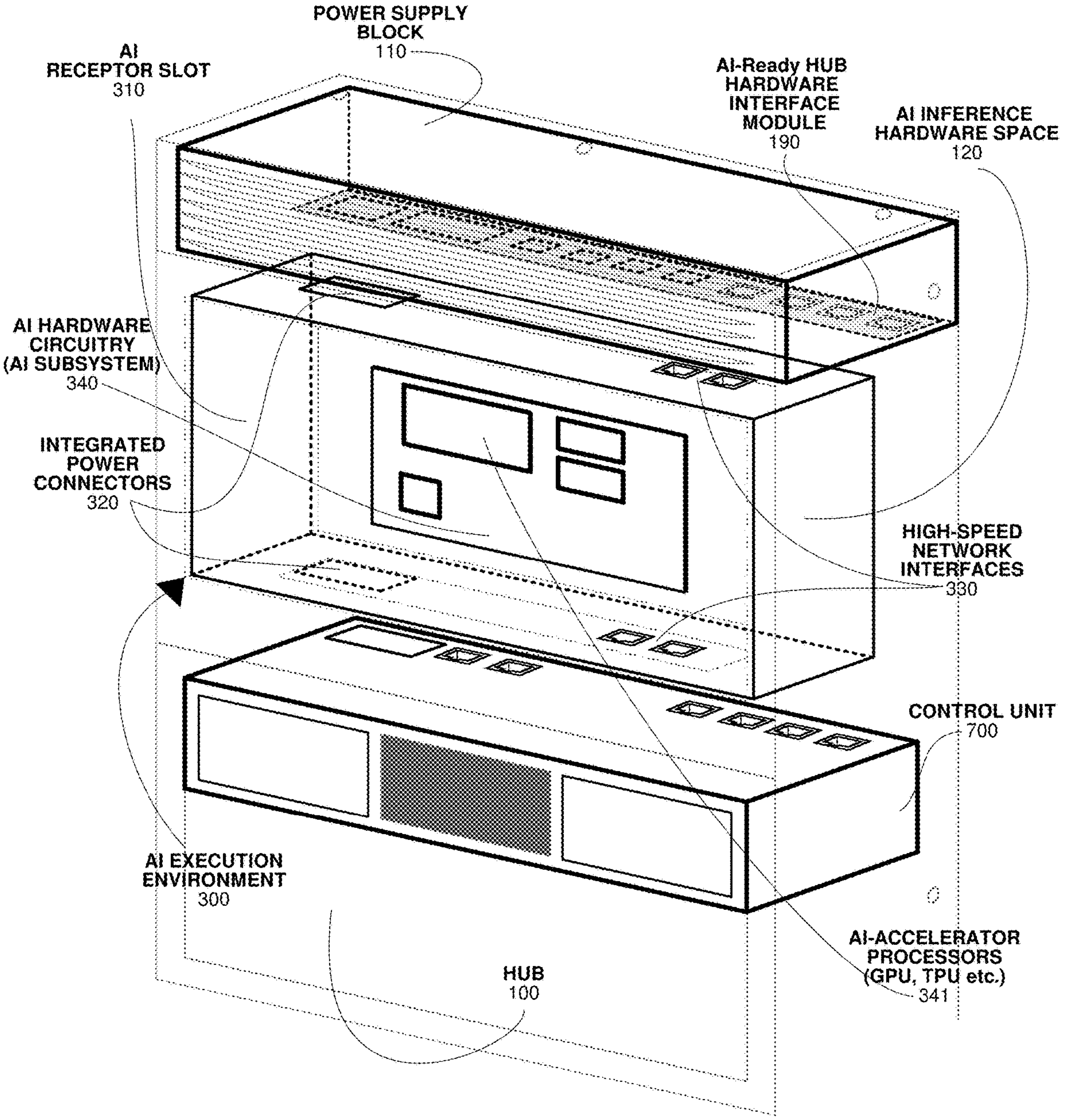
FIG. 3 shows the Artificial-Intelligence Execution Environment (300) in greater detail, illustrating the placement of the AI Receptor Slot (310), Integrated Power Connectors (320), High-Speed Network Interfaces (330), AI Hardware Circuitry (340), and associated accelerator processors within the hub's internal framework.

Referring now to FIG. 3, the drawing illustrates the Artificial-Intelligence Execution Environment (300) and its physical and logical integration within the AI-Ready Hub (100). The view emphasizes the relationship between the AI-specific components, the Control Unit (700), and the mandatory power and communication infrastructure that enable governance-controlled inference processing within the clinical environment.

At the upper portion of the figure, the Power Supply Block (110) and the AI-Ready Hub Hardware Interface Module (190) are shown as part of the Power Management Subsystem (500). These elements deliver isolated electrical power and backbone connectivity to the AI subsystem through integrated connectors (320) while maintaining compliance with IEC 60601-1 safety requirements. The AI Receptor Slot (310) provides a standardized mechanical and electrical docking region within the AI Inference Hardware Space (120) for installation of the AI module assembly.

Located within this space, the AI Hardware Circuitry (340)—collectively referred to as the AI Subsystem (340)—contains dedicated AI-accelerator processors (341) such as GPUs, TPUs, or equivalent parallel-processing units. These accelerators execute local inference workloads, feature extraction, and context evaluation based on data acquired from connected medical devices, sensors, or patient-facing interfaces. High-speed network interfaces (330) link the AI subsystem (340) to the Control Unit (700) and to the internal backbone established by modules (190) and (795), ensuring low-latency data flow between computational, compliance, and communication domains.

The AI Execution Environment (300) integrates firmware and middleware required to schedule, monitor, and validate AI operations within the compliance-controlled framework of the hub. It exchanges encrypted data and command packets with the AI-Ready Hub Software Interface Module (795) inside the Control Unit (700), while all execution events, model updates, and output renderings are verified and logged by the Compliance and Governance Subsystem (780). Power delivery and telemetry for the AI hardware are managed through the AI-Ready Hub Hardware Interface Module (190), which also provides galvanic isolation and network-level protection.

Through this integrated arrangement, the Artificial-Intelligence Execution Environment (300) operates as a local, deterministic inference platform directly embedded within the AI-Ready Hub (100). It enables regulated AI processing at the point of care while maintaining continuous synchronization with the internal backbone and the governance infrastructure that ensure transparency, traceability, and operational safety.

Referring now to FIG. 4, the illustration depicts the Patient Association and Credentialing Architecture (400) integrated within the AI-Ready Hub (100). The figure demonstrates how the Control Unit (700) and its communication interfaces enable secure identification, association, and interaction between a patient, the clinical information system, and connected medical or informational services operating under governance control.

The Control Unit (700) incorporates three dedicated communication windows. The Identifier Display and Optical Scanning Window (790) provides a front-facing interface for barcode, QR, or other optical codes used for credential presentation and secure device linking. The Short-Range Wireless Interface Window (792) supports RFID, NFC, Bluetooth®, or short-range Wi-Fi pairing for bedside association of wearable or handheld devices. The Long-Range Wireless Interface Window (794) extends connectivity beyond the patient room, enabling continuous communication through hospital Wi-Fi, LTE, or 5 G networks for telemedicine, data synchronization, and secure remote access to hospital systems.

A Patient Association Mechanism (400) establishes a verified linkage between the hub and a specific patient. In one embodiment, the association may be created through a Bracelet (410) equipped with RFID, NFC, or Bluetooth transceivers that communicate with the short-range interface. Alternatively, a Smartphone (420) running a secure companion application may pair with the hub through NFC, Bluetooth, or QR code scanning. Additional embodiments may employ a Biometric Credential (430)—including fingerprint, facial, voice, or retinal recognition-either through the hub itself or through an associated device. When identifiers are presented, the hospital information system (HIS) performs verification according to institutional Positive Patient Identification (PPID) and Admission/Discharge/Transfer (ADT) procedures. Upon successful validation, the Compliance and Governance Subsystem (780) issues a governance token that authorizes individualized hub access and scopes all subsequent activities to the authenticated patient identity.

Once association is established, the patient gains access to the Patient-Facing Information and Services Platforms (440) managed by the Patient-Facing Information and Services Subsystem (PF-CSS 250). These platforms provide clinical education, telehealth sessions, consent management, adherence monitoring, secure payment services (450), and optional entertainment features. Additional interfaces include Remote Control Functions (460) that permit patients to navigate or command hub services, and Communication Options (470) such as voice, VOIP, SIP, or intercom endpoints that enable bidirectional communication between patients and clinical staff. The system also integrates a Nurse Call System (480), allowing authenticated assistance requests to be initiated directly from the hub while maintaining interoperability with existing hospital communication infrastructure.

All association events and subsequent user interactions are mediated through the AI-Ready Hub Software Interface Module (795), verified by the Compliance and Governance Subsystem (780), and permanently recorded in the compliance ledger to ensure full traceability and regulatory conformity. Patient credentials and governance tokens remain active only for the duration of the authenticated session and are automatically revoked upon discharge, reassignment, or bracelet removal. Successor identification and authentication methods—including emerging biometric standards, advanced wireless protocols, or new hospital interoperability frameworks—are expressly contemplated within the scope of the described patient-association architecture.

Figure 5:
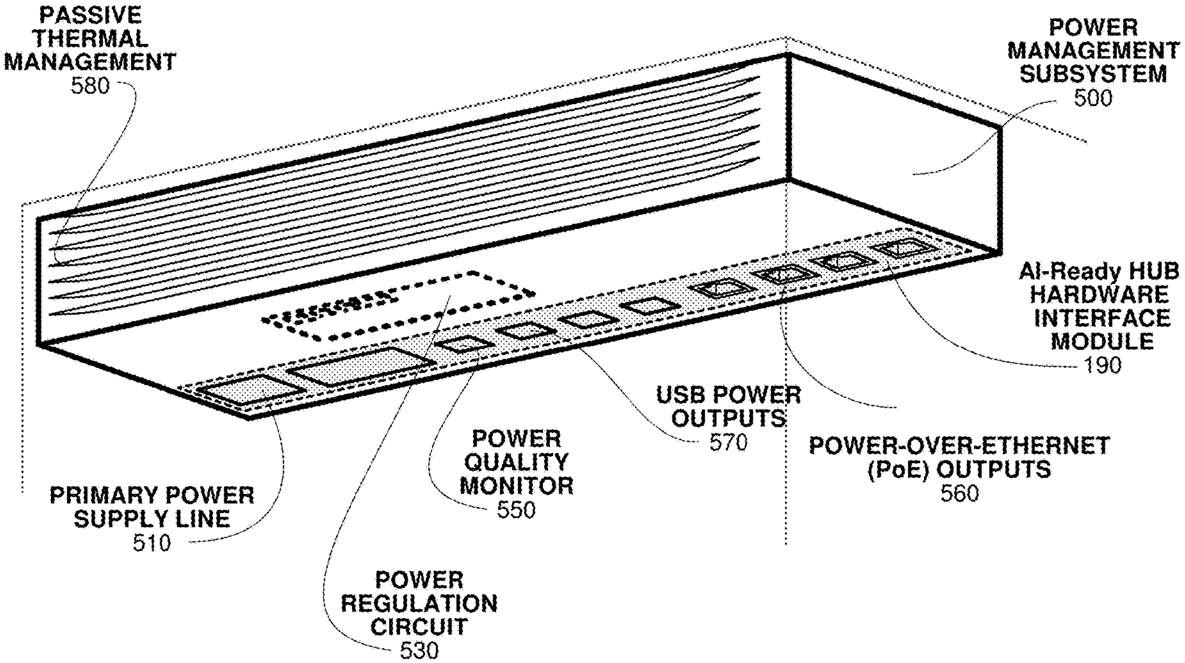
FIG. 5 illustrates the Power Management Subsystem (500), detailing the flow of electrical energy through the Primary Power Supply Line (510), Power Regulation Circuit (530), Power Quality Monitor (550), PoE Outputs (560), USB Power Outputs (570), and Passive Thermal Management (580) under supervision of the AI-Ready Hub Hardware Interface Module (190).

Referring now to FIG. 5, the drawing illustrates the Power Management Subsystem (500) of the AI-Ready Hub (100), showing how regulated electrical power and network energy distribution are managed within a compliance-controlled infrastructure. The figure emphasizes the pathways through which power is received, conditioned, monitored, and delivered to other subsystems of the hub, including the Control Unit (700), the Artificial-Intelligence Execution Environment (300), and the Patient-Facing Subsystem (250).

At the entry point of the subsystem, a Primary Power Supply Line (510) provides the main electrical input from external sources such as hospital AC mains, Power-over-Ethernet (PoE), or USB-C inlets. The incoming current is first routed through the AI-Ready Hub Hardware Interface Module (190), which functions as the unified electrical and network ingress. Within the Power Management Subsystem (500), the input is processed by a Power Regulation Circuit (530) that converts and isolates voltage levels to meet the medical-grade requirements of IEC 60601-1, ensuring patient and operator safety.

Downstream of the regulation stage, a Power Quality Monitor (550) continuously samples current, voltage, and frequency parameters, verifying stability and integrity of the supplied energy. Telemetry from the monitor (550) is transmitted in real time to the Control Unit (700) through the AI-Ready Hub Software Interface Module (795), where it is analyzed by the Compliance and Governance Subsystem (780). Any deviation from permitted thresholds-such as transient spikes, leakage currents, or load imbalance-triggers corrective isolation and produces a compliance-ledger entry to preserve a verifiable audit trail of power safety.

The regulated outputs of the subsystem are distributed through multiple channels. Dedicated Power-over-Ethernet (POE) Outputs (560) supply both energy and network connectivity to associated hub modules, while USB Power Outputs (570) provide low-voltage power for accessory or peripheral devices. Each output channel incorporates overcurrent protection and galvanic isolation barriers, permitting modular attachments to be safely energized or disconnected under software supervision. Load negotiation and allocation are coordinated across the internal backbone, allowing the Control Unit (700) to dynamically manage power delivery according to operational demand and policy constraints.

Thermal stability of the subsystem is maintained through a Passive Thermal Management structure (580) integrated along the upper portion of the housing. This structure employs conductive heat spreaders and convective venting to dissipate waste heat without reliance on active fans, preserving acoustic neutrality and long-term reliability in clinical environments. Temperature data are incorporated into the same telemetry stream monitored by the Compliance and Governance Subsystem (780), ensuring that thermal performance is continuously validated alongside electrical safety metrics.

Accordingly, FIG. 5 demonstrates how the Power Management Subsystem (500) integrates the Primary Power Supply Line (510), Power Regulation Circuit (530), Power Quality Monitor (550), PoE Outputs (560), USB Power Outputs (570), and Passive Thermal Management (580) within a single, auditable power architecture. Operating through the AI-Ready Hub Hardware Interface Module (190) and under supervision of the Compliance and Governance Subsystem (780), this subsystem ensures that every electrical transaction within the AI-Ready Hub (100) remains safe, traceable, and compliant with institutional and regulatory standards.

Referring now to FIG. 6, the illustration depicts the Compliance and Governance Subsystem (600) that governs validation, ledgering, and audit functions across all operational domains of the AI-Ready Hub (100). The subsystem executes within the Control Unit (700) as part of the secure firmware and software layer (780) responsible for enforcing institutional, regulatory, and technical governance rules. FIG. 6 outlines the logical sequence through which policy definitions are applied, transactions are validated, events are cryptographically secured, and compliance feedback is maintained.

At the initiation stage, operational events generated by the hub's subsystems are received by the Validation Component (610). This component evaluates each event against compliance policies stored within a Policy Store (612)—a protected repository that contains machine-readable rules, access permissions, and configuration constraints derived from institutional and regulatory frameworks. Validation operates under a Deny-by-Default Gate (614), which enforces a conservative posture by blocking any data transmission, device command, or configuration change unless all applicable criteria are satisfied. This architecture ensures that governance control is proactive and continuous rather than reactive.

Once an event satisfies validation conditions, the subsystem generates corresponding Ledger Entries (620) that record the verified action in structured, tamper-resistant form. Each ledger record is then processed through a Cryptographic Signing Stage (630) that applies asymmetric or certificate-based digital signatures to guarantee authenticity and non-repudiation. Signed entries are subsequently incorporated into a Blockchain Anchoring Module (640), which embeds hashes or transaction identifiers into a distributed or immutable ledger structure. This mechanism establishes permanent, verifiable traceability for all compliance-relevant operations performed within the hub.

An Audit and Compliance Feedback Loop (670) continuously monitors the ledger and operational telemetry to detect anomalies, deviations from policy, or performance irregularities. When discrepancies are identified, the feedback loop communicates corrective instructions to the Validation Component (610), initiating dynamic policy adjustment or subsystem intervention. This closed-loop control enables the compliance framework to evolve in real time and to sustain long-term regulatory alignment across firmware updates, configuration changes, and multi-institutional deployments.

Through the coordinated operation of components 610, 612, 614, 620, 630, 640, and 670, the Compliance and Governance Subsystem (600) provides an end-to-end assurance chain for the AI-Ready Hub (100). It validates every event before execution, records each authorized action as a signed ledger entry, anchors those entries in an immutable data structure, and maintains a feedback channel for continuous auditability. In doing so, the subsystem forms the core of the hub's verifiable trust model, ensuring that every computation, communication, and control flow remains accountable and compliant within the governed clinical environment.

Figure 7:
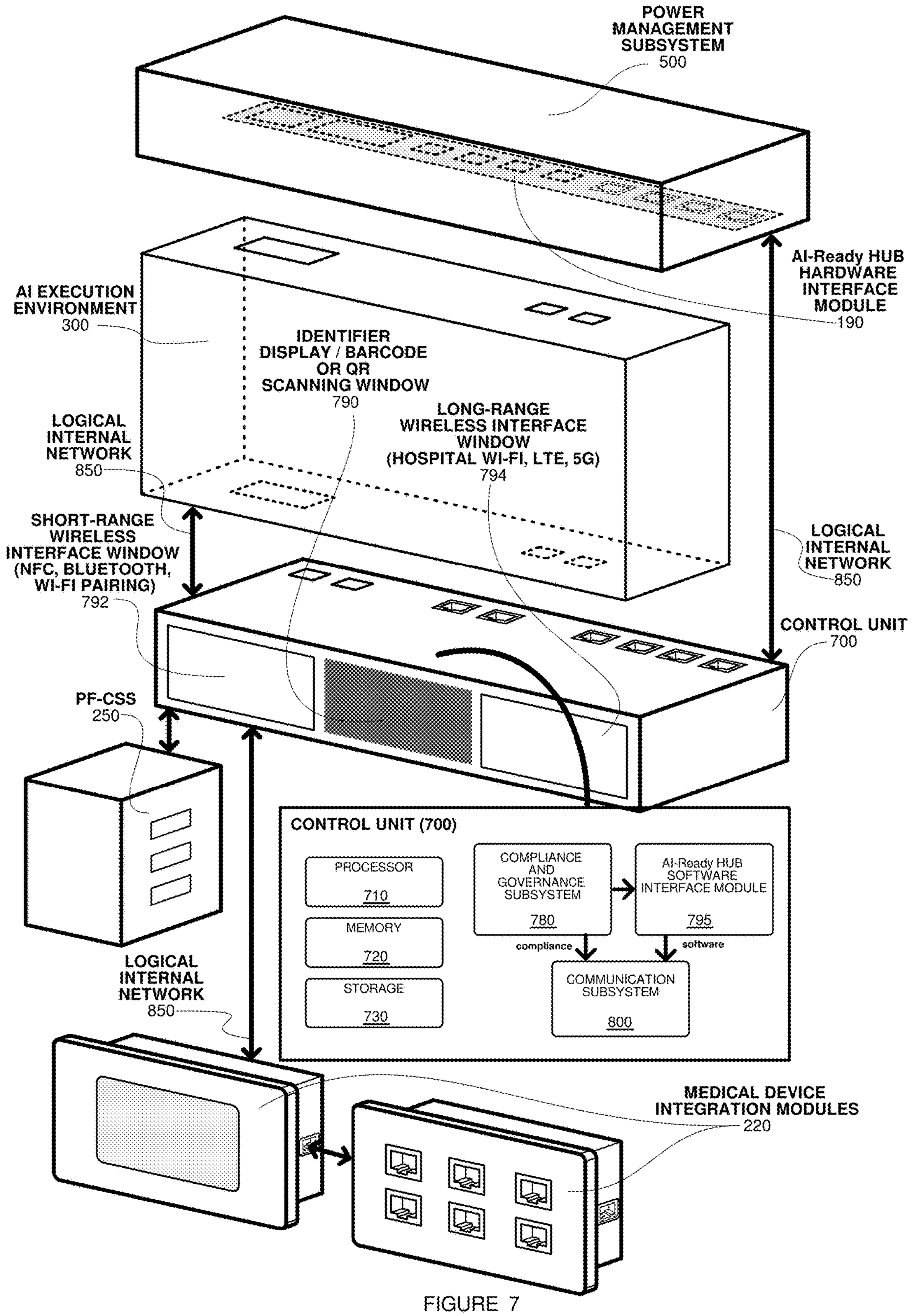
FIG. 7 illustrates the Control Unit (700) and its internal architecture, including the Processor (710), Memory (720), Storage (730), Compliance and Governance Subsystem (780), AI-Ready Hub Software Interface Module (795), and Communication Subsystem (800) interconnected through the Logical Internal Network (850) to other hub components.

Referring now to FIG. 7, the illustration depicts the Control Unit (700) and its associated Logical Internal Network (850) as central elements of the AI-Ready Hub (100). The figure demonstrates the physical and logical interconnections between the hub's power, communication, artificial-intelligence, and patient-facing subsystems, emphasizing the manner in which compliance, governance, and data exchange are coordinated within the regulated infrastructure.

At the upper portion of the figure, the Power Management Subsystem (500) delivers regulated electrical power and backbone connectivity through the AI-Ready Hub Hardware Interface Module (190). This ingress path establishes the primary electrical and data link into the Control Unit (700), providing the foundation for both operational energy distribution and network synchronization. The Artificial-Intelligence Execution Environment (300) is shown adjacent to the power subsystem, indicating its direct coupling to the Control Unit (700) for inference processing and compliance-supervised data flow.

Within the Control Unit (700), core computing elements include at least one Processor (710), system Memory (720), and non-volatile Storage (730) containing firmware and executable instructions that implement orchestration, subsystem coordination, and governance-enforcement logic. The processor executes embedded control code responsible for managing connected modules, validating data exchanges, and enforcing power, safety, and communication policies as specified by the hub's governance framework.

Integrated within the Control Unit (700) is the Compliance and Governance Subsystem (780), a secure hardware-assisted software layer configured to manage policy evaluation, event validation, and compliance ledger recording. Adjacent to subsystem (780) is the AI-Ready Hub Software Interface Module (795), which governs discovery, routing, and authentication across all internal communication paths. The Software Interface Module (795) supervises the Communication Subsystem (800)—also resident within the Control Unit (700)—which provides the physical and logical network interfaces connecting the hub to hospital infrastructure and external systems. The Communication Subsystem (800) includes short-range and long-range wireless components represented by the Short-Range Wireless Interface Window (792) and the Long-Range Wireless Interface Window (794), enabling both local and wide-area connectivity under continuous compliance supervision.

A third communication surface, the Identifier Display and Scanning Window (790), supports visual and optical credential operations such as barcode, QR, or identifier code presentation for patient and device association, as described in FIG. 4. All three interface windows 790, 792, and 794 operate under control of the Compliance and Governance Subsystem (780) and are coordinated through the Software Interface Module (795), ensuring that every communication event is validated, logged, and cryptographically secured.

The Logical Internal Network (850), illustrated by dashed interconnection lines, provides the internal communication fabric linking the Control Unit (700) to other subsystems of the hub. Through this network, bidirectional data and governance signals are exchanged between the Control Unit (700), the Power Management Subsystem (500), the AI Execution Environment (300), the Patient-Facing Information and Services Subsystem (PF-CSS 250), and the Medical Device Integration Modules (220). The network (850) carries both operational and compliance data, enabling deterministic orchestration of power, inference, and patient-interaction functions while maintaining strict policy enforcement through subsystem (780).

Each connected module—whether a patient-facing tablet (250) or a medical device interface unit (220)—communicates through the Logical Internal Network (850) under management of the Software Interface Module (795). The Communication Subsystem (800) mediates between the internal backbone and external networks, ensuring that all transmissions remain cryptographically signed, audit-tracked, and policy-constrained in accordance with institutional and regulatory standards.

Accordingly, FIG. 7 illustrates how the Control Unit (700) operates as the central orchestration and compliance core of the AI-Ready Hub (100). By integrating the processor (710), memory (720), storage (730), compliance subsystem (780), software interface module (795), and communication subsystem (800) within a unified architecture, and by interconnecting all subsystems through the Logical Internal Network (850), the Control Unit provides deterministic control, secure interoperability, and continuous governance across every aspect of hub operation.

Referring now to FIG. 8, the drawing illustrates the Communication Subsystem (800) of the AI-Ready Hub (100) and its role as the primary data-exchange framework connecting internal hub components with patient devices and external hospital infrastructure. The figure depicts the hierarchical network topology through which the hub enables secure communication across short-range, private, and wide-area domains under compliance supervision.

The Communication Subsystem (800) operates within the Control Unit (700) and is governed by the Compliance and Governance Subsystem (780) through the AI-Ready Hub Software Interface Module (795). It integrates multiple communication layers, including a Personal Area Network (PAN 810) for short-range pairing, a Private Wi-Fi Network (820) for patient-specific connectivity, a Virtual Private Network (VPN 830) for secure vendor and telemedicine tunnels, and a 5 G/LTE Cellular Interface (840) for redundant long-range access. Each of these layers is instantiated within the subsystem under centralized policy control to ensure encryption, authentication, and audit-ready data flow.

At the hardware level, communication channels are realized through the Short-Range Wireless Interface Window (792) and the Long-Range Wireless Interface Window (794). The short-range interface supports NFC, Bluetooth®, and local Wi-Fi pairing for patient-worn or bedside devices, while the long-range interface maintains continuous network linkage through hospital Wi-Fi, LTE, or 5 G domains. Both interfaces are validated and managed by the Compliance Subsystem (780) to guarantee that all transmissions adhere to approved governance policies.

The subsystem (800) also maintains persistent links to the AI Subsystem (340), which processes data and generates context-aware responses, and to the Patient-Facing Information and Services Subsystem (PF-CSS 250), which delivers personalized clinical, educational, and communication services to the authenticated patient. Bidirectional channels further extend to the Medical Device Subsystem (740), enabling deterministic exchange of device telemetry, status updates, and control instructions between the hub and attached medical equipment. All such communications traverse the Logical Internal Network (850) defined in FIG. 7, ensuring synchronized data governance and system awareness.

Externally, the Communication Subsystem (800) interfaces with the Hospital Network, Cloud, or Electronic Health Record (EHR) Infrastructure (860), supporting standards-compliant exchange of clinical data, teleconsultation streams, and audit metadata. Secure connections are established using VPN (830) and cellular (840) tunnels to extend hub functionality beyond the facility when authorized. On the patient side, the subsystem supports integration with Patient Devices (870), including smartphones, tablets, control remotes, or identification bracelets that participate in the patient-association framework described in FIG. 4. These devices connect through the PAN (810) or private Wi-Fi (820) channels, enabling authenticated, policy-enforced communication under the same governance scope as internal modules.

Through these integrated communication layers, the Communication Subsystem (800) establishes a unified, compliance-monitored networking environment that bridges patient-facing, medical-device, and institutional domains. Every transmission—whether short-range, local, or wide-area—is validated, encrypted, and logged through the Compliance and Governance Subsystem (780), ensuring that data integrity, privacy, and traceability are continuously preserved across the entire AI-Ready Hub (100) ecosystem.

Referring now to FIG. 9, the illustration presents a representative Patient Room Use Case (900) showing the integrated operation of the AI-Ready Hub (100) within a clinical environment. The figure demonstrates how medical devices, patient-facing interfaces, wearable credentials, and compliance systems interact to form a continuous, governance-controlled care ecosystem.

The AI-Ready Hub (100) is mounted on the room wall and functions as the operational and compliance nucleus. Within the hub, the Control Unit (700) and Compliance Subsystem (600) coordinate all connected subsystems through the Logical Internal Network (850). The AI Subsystem (340) executes local inference workloads, enabling real-time analysis of device telemetry and patient interaction events under active governance supervision.

In this embodiment, the hub interfaces with multiple bedside and personal devices. A Bracelet (410) worn by the patient serves as a secure credential token, equipped with NFC, Bluetooth®, or RFID capabilities for proximity-based identification. The bracelet communicates with a Bracelet Dock (910) linked to the hub, automatically establishing association when the patient enters or occupies the assigned bed space. This identification is cross-validated through the Compliance Subsystem (600) and recorded as a signed ledger entry, ensuring traceable patient linkage and session integrity.

Medical devices such as an Infusion Pump (920) and a Patient Monitor (930) connect through the Medical Device Integration Modules (220). These modules interface bi-directionally with the Control Unit (700), transmitting telemetry data for local validation and AI-assisted interpretation within the AI Subsystem (340). All device operations-start, stop, dosage adjustments, and alarm events—are governed by policy enforcement rules, with compliance status and results logged to the immutable ledger managed by subsystem (600).

The Patient-Facing Information and Services Subsystem (PF-CSS 250) provides the interactive layer between the patient and the hub. It may appear as an integrated tablet or wall display positioned near the patient bed, delivering educational material, consent workflows, adherence guidance, or entertainment services validated by the Compliance Subsystem (600). Each interaction performed through the PF-CSS generates a corresponding ledger record to maintain verifiable accountability.

External communication pathways are represented by the Communication Option (470), such as a handset, intercom, or VOIP endpoint, and by the patient's Smartphone (420) paired to the hub through secure short-range protocols. Both devices allow authenticated calls, telemedicine sessions, or control commands routed through the Communication Subsystem (800). The Nurse Call System (480) is integrated within this same communication network, enabling assistance requests or alarm notifications to be transmitted directly to clinical staff while maintaining compliance logging.

All functional interactions shown in FIG. 9—including bracelet association, device telemetry, AI inference, patient education, and nurse-call signaling—are continuously monitored and verified by the Compliance Subsystem (600). Each validated event produces a cryptographically signed ledger entry within the governance infrastructure, forming a complete audit trail of clinical and technical activity. The combined operation of the AI Subsystem (340), PF-CSS (250), Medical Device Modules (220), and Compliance Subsystem (600) under the orchestration of the Control Unit (700) demonstrates a secure, intelligent, and policy-aware patient-care environment.

Accordingly, FIG. 9 exemplifies the holistic integration of artificial-intelligence processing, device interoperability, patient identification, and compliance governance within the AI-Ready Hub (100) framework, providing continuous, auditable assurance of safety, privacy, and operational integrity in bedside clinical use.

Figure 10:
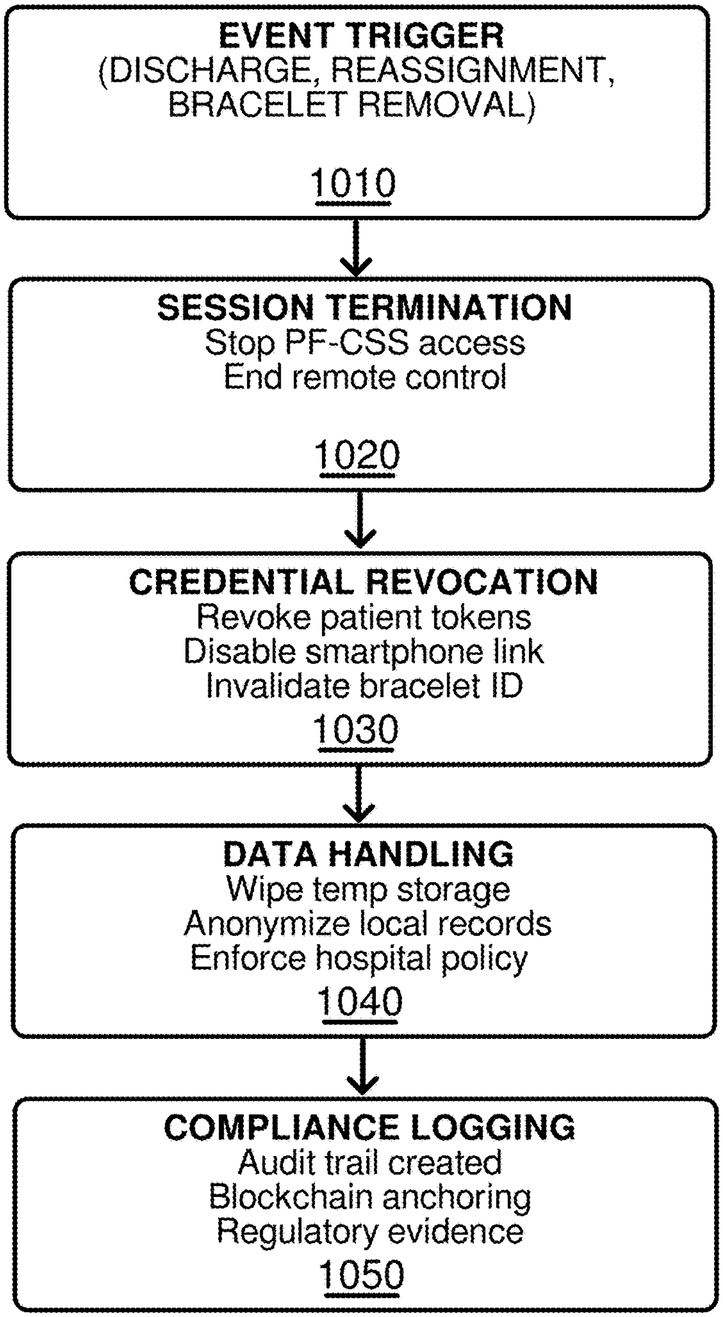
FIG. 10 depicts the Session Termination and Credential Revocation Sequence (1000), outlining the secure operational stages of Event Trigger (1010), Session Termination (1020), Credential Revocation (1030), Data Handling (1040), and Compliance Logging (1050) managed by the Compliance and Governance Subsystem (600) to maintain audit-ready governance continuity.

Referring now to FIG. 10, the illustration depicts the Session Termination and Credential Revocation Sequence (1000), which governs how patient access, data retention, and compliance recording are managed when a session concludes within the AI-Ready Hub (100). The sequence ensures that all authentication tokens, stored data, and connected services are securely deactivated in accordance with institutional and regulatory policy, maintaining full auditability through the Compliance and Governance Subsystem (600).

The process begins with an Event Trigger (1010), which may include patient discharge, bed reassignment, or bracelet removal detected by the hub's patient-association mechanism described in FIG. 4. Upon detection of such an event, the system initiates an orderly shutdown of all patient-specific functions.

In the next stage, Session Termination (1020), the hub disables access to the Patient-Facing Information and Services Subsystem (PF-CSS 250) and ends any remote-control or telehealth session established through the Communication Subsystem (800). Active data streams from patient devices or medical modules are gracefully closed, and any pending inference tasks in the AI Subsystem (340) are halted or quarantined pending policy validation.

Following session termination, the system proceeds to Credential Revocation (1030). In this phase, all digital identifiers linked to the authenticated patient are invalidated. This includes revoking patient tokens issued by the governance subsystem, disabling smartphone or wearable links, and rendering the Bracelet (410) or associated identifier inoperable. These actions ensure that no lingering credentials can be reused or spoofed once the patient is discharged or moved.

Once credentials are revoked, the sequence advances to Data Handling (1040), where all temporary or session-specific data are securely processed. The hub wipes transient storage, anonymizes any locally cached patient records, and enforces data-retention policies defined by hospital governance. Data that must be preserved for audit or legal compliance is transferred into protected storage under encryption and metadata tagging, ensuring that personal identifiers are no longer accessible.

Finally, the process concludes with Compliance Logging (1050). At this stage, all termination and revocation events are written into the compliance ledger maintained by the Compliance and Governance Subsystem (600). Each log entry is cryptographically signed, time-stamped, and anchored into the immutable blockchain structure (640) described in FIG. 6, generating a permanent regulatory evidence trail. These records verify that access was revoked, data was sanitized, and all operations were performed in conformance with approved policy.

Through these sequential stages-event detection, session termination, credential revocation, secure data handling, and compliance logging—the Session Termination and Credential Revocation Sequence (1000) provides a complete, auditable framework for ending patient interactions with the AI-Ready Hub (100). It ensures that clinical data integrity, privacy, and governance continuity are maintained throughout the entire operational lifecycle, even beyond the point of patient discharge.

The invention claimed is:

1. An integrated clinical infrastructure hub configured for installation within or on a wall of a healthcare environment, the hub comprising:

(a) a power-management subsystem comprising a primary power module configured to receive or deliver regulated electrical power through one or more medically isolated power interfaces selected from Power-over-Ethernet, PoE++, USB-C power delivery, AC mains power, and regulated DC power, the power-management subsystem being configured to monitor at least one of voltage, current, thermal condition, load state, or power-source status;

(b) a modular chassis comprising a modular receptor assembly having a plurality of standardized outlet spaces configured to receive interchangeable modules, the interchangeable modules comprising one or more of:

(i) a medical-device integration module configured to receive sensor data, device data, or vendor-specific medical-device communications from at least one connected medical device;

(ii) an artificial-intelligence accelerator module comprising dedicated artificial-intelligence hardware circuitry configured to execute artificial-intelligence or machine-learning workloads within a patient-care environment;

(iii) a patient-facing service module or tablet interface configured to provide authenticated patient-facing services; and (iv) a nurse-call module, clinical-signaling module, standard electrical outlet module, communication module, or protective cover;

(c) a communication subsystem configured to communicatively couple the hub to one or more of a connected medical device, a patient-facing endpoint, a hospital information system, an electronic health record system, a remote computing system, or a clinical notification system;

(d) an artificial-intelligence execution environment communicatively coupled to the modular receptor assembly and configured to perform local artificial-intelligence inference, rule-based analysis, or delegated artificial-intelligence execution using the artificial-intelligence accelerator module or a remote computational resource;

(e) a patient-facing subsystem configured to provide one or more authenticated patient-facing services selected from telehealth communication, consent management, adherence support, education, entertainment, secure payment, patient identification, or patient-session management;

(f) a compliance-governance subsystem comprising a policy store, a validation component, a deny-by-default gate, and a compliance ledger; and (g) a control unit comprising at least one processor, memory communicatively coupled to the at least one processor, and a non-transitory computer-readable storage medium storing instructions that, when executed by the at least one processor, cause the control unit to:

(i) receive medical-device data from the medical-device integration module, patient-associated data from the patient-facing subsystem, operational data from the power-management subsystem, and communication-state data from the communication subsystem;

(ii) validate the received medical-device data, patient-associated data, operational data, and communication-state data against one or more compliance policies stored in the policy store;

(iii) generate or revoke governance tokens controlling access to data exchange, patient-facing services, artificial-intelligence execution, power-state control, clinical signaling, or external-system communication;

(iv) block release of data, execution of control commands, activation of patient-facing services, or transmission of clinical notifications unless validation by the compliance-governance subsystem succeeds;

(v) record validation events, governance-token events, power-management events, patient-association events, artificial-intelligence execution events, clinical-signaling events, and external-communication events as compliance-controlled entries in the compliance ledger; and (vi) coordinate operation of the medical-device integration module, the artificial-intelligence execution environment, the patient-facing subsystem, the communication subsystem, and the power-management subsystem through the compliance-governance subsystem;

wherein the hub provides a unified, compliance-governed clinical infrastructure platform in which medical-device integration, artificial-intelligence execution, patient-facing services, communication, and regulated power management are controlled through governance-token authorization, deny-by-default validation, and compliance-ledger recording.

2. The hub of claim 1, wherein the control unit is further configured to perform predictive maintenance by analyzing power consumption, thermal load, power-source status, and subsystem performance metrics, and by recording a compliance-controlled entry in the compliance ledger when the analyzed metrics indicate a deviation from a permitted operating threshold.

3. The hub of claim 1, wherein the patient-facing subsystem comprises a tablet computer or patient-facing service module executing hospital-authorized software, the tablet computer or patient-facing service module being cryptographically bound to the compliance-governance subsystem and configured to provide telehealth communication, consent management, adherence tracking, secure payment, education, or entertainment services under issuance of a governance token, with each patient-facing interaction recorded as a compliance-controlled entry in the compliance ledger.

4. The hub of claim 1, wherein the compliance ledger is configured to anchor compliance-controlled entries in a cryptographically verifiable, tamper-evident data structure selected from a blockchain, a distributed ledger, a hash-chain ledger, or an immutable audit-record framework.

5. The hub of claim 1, wherein the deny-by-default gate is configured to withhold release of data, execution of control commands, activation of patient-facing services, or transmission of clinical notifications until validation by the compliance-governance subsystem succeeds.

6. The hub of claim 1, further comprising a secure timebase synchronized by authenticated Network Time Protocol, Precision Time Protocol, or Global Navigation Satellite System timing signals, wherein timestamps generated from the secure timebase are cryptographically bound to compliance-controlled entries recorded in the compliance ledger.

7. The hub of claim 1, wherein the communication subsystem is configured to perform automated network validation across wired or wireless communication interfaces selected from Ethernet, Wi-Fi, cellular, optical, Bluetooth Low Energy, Ultra-Wideband, Radio-Frequency Identification, Near-Field Communication, or USB-C communication interfaces, and wherein the automated network validation comprises measuring throughput, latency, jitter, packet-loss performance, or link-authentication status and recording resulting network-validation metrics in the compliance ledger.

8. The hub of claim 1, wherein the communication subsystem is configured to interface with a real-time location service infrastructure using one or more positioning or proximity technologies selected from Bluetooth Low Energy, Ultra-Wideband, Radio-Frequency Identification, optical tracking, magnetic positioning, acoustic ranging, Near-Field Communication, or machine-readable optical code scanning, and to associate spatial or contextual metadata with device records, patient records, or compliance-controlled entries in the compliance ledger.

9. The hub of claim 1, wherein patient credentials, module credentials, subsystem credentials, or governance-token credentials are anchored to a hardware security module, and wherein provenance fields recorded in the compliance ledger identify a hub identity, module identity, active policy version, or patient-session identifier.

10. The hub of claim 1, wherein the patient-facing subsystem is configured to automatically revoke or delete patient credentials upon disassociation, expiration, invalidation of an authenticated patient identifier, patient discharge, or patient reassignment, the authenticated patient identifier comprising a wearable bracelet, biometric credential, smart card, mobile device, or electronic patient token.

11. The hub of claim 1, wherein the compliance-governance subsystem is configured to synchronize selected compliance-ledger entries with one or more additional hubs across healthcare, institutional, or home-care locations to form a federated governance network that supports distributed validation, cross-site auditability, policy harmonization, inter-facility coordination, regulatory oversight, or longitudinal compliance assurance.

12. The hub of claim 1, further comprising a patient-association mechanism configured to authenticate, bind, and manage an association between the hub and an identified patient, user, client, or monitored individual, the patient-association mechanism using one or more communication interfaces selected from Bluetooth Low Energy, Near-Field Communication, Radio-Frequency Identification, optical code scanning, barcode scanning, QR-code scanning, biometric sensing, or smart-card communication, and being configured to issue, refresh, or revoke governance tokens controlling individualized access to patient-facing services or device-specific functions, with authentication, association, disassociation, token-issuance, token-refresh, and token-revocation events recorded as compliance-controlled entries in the compliance ledger.

13. The hub of claim 1, wherein the artificial-intelligence execution environment is configured to generate an artificial-intelligence inference or rule-based analysis indicating patient deterioration, and wherein the compliance-governance subsystem is configured to validate the artificial-intelligence inference or rule-based analysis before triggering a nurse-call alert or clinical notification.

14. The hub of claim 1, wherein, upon network disruption, the control unit is configured to cache validated data locally and resynchronize the cached validated data with the compliance ledger upon reconnection, thereby maintaining continuity of compliance records.

15. The hub of claim 1, wherein the control unit is configured to manage a quality-of-service framework that prioritizes real-time clinical data streams, medical-device alerts, nurse-call alerts, or validated patient-safety notifications over non-critical patient-facing service traffic.

16. The hub of claim 1, wherein the communication subsystem comprises at least one routing, gateway, or intermediary communication device deployed within a healthcare facility, patient home, ambulatory setting, or remote-care environment, the routing, gateway, or intermediary communication device being configured to connect the hub with institutional systems comprising hospital-information systems, control systems, communication systems, alarm systems, governance systems, or data-management systems, and with patient-facing systems comprising tablets, mobile devices, software applications, or patient-facing endpoints, over wired, wireless, optical, or hybrid networks using one or more communication standards selected from Ethernet, Wi-Fi, cellular, satellite, optical, Bluetooth Low Energy, Ultra-Wideband, Radio-Frequency Identification, Near-Field Communication, or USB-C communication interfaces, and being further configured to manage, normalize, and validate bidirectional data exchanges among the hub, institutional infrastructure, and patient-facing systems, with each validated exchange recorded as a compliance-controlled entry in the compliance ledger.

17. The hub of claim 1, wherein the patient-facing subsystem is enabled only upon issuance of a governance token, and wherein each patient session is recorded as a compliance-controlled entry in the compliance ledger.

18. The hub of claim 1, wherein the medical-device integration module is configured to receive data from an IV pole, infusion pump, patient monitor, sensor, ventilator, laboratory device, or bedside medical device, and wherein received outputs are validated by the compliance-governance subsystem and recorded in the compliance ledger under governance-token control.

19. The hub of claim 1, wherein the artificial-intelligence execution environment is configured to selectively delegate or distribute artificial-intelligence inference execution to one or more remote computational nodes within a federated, institutional, or cloud-based infrastructure, and wherein returned inference results are validated, cryptographically signed, and recorded as compliance-controlled entries in the compliance ledger.

20. A method of operating an integrated clinical infrastructure hub installed within or on a wall of a healthcare environment, the hub comprising a power-management subsystem, a modular receptor assembly, a medical-device integration module, an artificial-intelligence execution environment, a patient-facing subsystem, a communication subsystem, a compliance-governance subsystem, and a control unit, the method comprising:

(a) receiving, by the control unit, medical-device data from one or more connected medical devices through the medical-device integration module;

(b) receiving, by the control unit, patient-associated data from the patient-facing subsystem, the patient-associated data being associated with an authenticated patient identifier or an authenticated patient session;

(c) receiving, by the control unit, operational data from the power-management subsystem, the operational data comprising at least one of voltage data, current data, thermal data, load-state data, power-source status data, or power-quality data;

(d) receiving, by the control unit, communication-state data from the communication subsystem, the communication-state data comprising at least one of link-state data, network-authentication data, latency data, packet-loss data, routing data, or external-system connection data;

(e) validating, by the compliance-governance subsystem, the medical-device data, the patient-associated data, the operational data, and the communication-state data against one or more compliance policies stored in a policy store;

(f) enforcing, by a deny-by-default gate of the compliance-governance subsystem, a default block against release of data, execution of control commands, activation of patient-facing services, artificial-intelligence execution, power-state control, clinical signaling, or external-system communication unless validation succeeds;

(g) generating, refreshing, or revoking governance tokens that define authorization conditions for at least one of data exchange, patient-facing service activation, artificial-intelligence execution, medical-device communication, power-state control, clinical signaling, or external-system communication;

(h) executing, within the artificial-intelligence execution environment, local artificial-intelligence inference or rule-based analysis using an artificial-intelligence accelerator module disposed within the hub, or delegating artificial-intelligence execution to a remote computational resource under authorization of a governance token;

(i) recording, in a compliance ledger, compliance-controlled entries corresponding to validation events, governance-token events, patient-association events, power-management events, medical-device communication events, artificial-intelligence execution events, clinical-signaling events, and external-communication events; and (j) coordinating operation of the medical-device integration module, the artificial-intelligence execution environment, the patient-facing subsystem, the communication subsystem, and the power-management subsystem through the compliance-governance subsystem so that medical-device integration, patient-facing services, artificial-intelligence execution, communication, and regulated power management are controlled through governance-token authorization, deny-by-default validation, and compliance-ledger recording.

21. The method of claim 20, further comprising synchronizing selected compliance-controlled entries of the compliance ledger with one or more additional integrated clinical infrastructure hubs across healthcare, institutional, home-care, ambulatory, or remote-care locations to form a federated governance network that supports distributed validation, cross-site auditability, policy harmonization, interfacility coordination, regulatory oversight, or longitudinal compliance assurance.

22. The method of claim 20, further comprising generating, by the artificial-intelligence execution environment, an artificial-intelligence inference or rule-based analysis indicating patient deterioration, validating the artificial-intelligence inference or rule-based analysis using the compliance-governance subsystem, and, after successful validation, generating a nurse-call alert or clinical notification.

23. The method of claim 20, further comprising authenticating and associating an identified patient, user, client, or monitored individual with the hub using a patient-association mechanism comprising one or more communication interfaces selected from Bluetooth Low Energy, Near-Field Communication, Radio-Frequency Identification, optical code scanning, barcode scanning, QR-code scanning, biometric sensing, smart-card communication, or mobile-device communication; issuing a governance token that enables individualized access to patient-facing services; refreshing or revoking the governance token upon disassociation, expiration, invalidation, patient discharge, or patient reassignment; and recording authentication, association, token-issuance, token-refresh, and token-revocation events as compliance-controlled entries in the compliance ledger.

24. The method of claim 20, further comprising selectively delegating execution of one or more artificial-intelligence models to one or more remote computational nodes within a federated, institutional, edge-computing, or cloud-based infrastructure; validating and cryptographically signing returned inference results; binding the returned inference results to an originating policy version, hub identity, module identity, patient-session identifier, or user context; and recording a corresponding inference transaction as a compliance-controlled entry in the compliance ledger.

25. The method of claim 20, further comprising associating real-time location metadata of patient wearables, medical devices, patient-facing endpoints, or hub-connected modules with validated data, patient records, device records, or compliance-controlled entries in the compliance ledger.

26. The method of claim 20, further comprising enabling the patient-facing subsystem only upon issuance of a governance token, recording patient-facing information sessions, patient-facing service sessions, telehealth sessions, consent-management sessions, adherence-support sessions, education sessions, entertainment sessions, or secure-payment sessions as compliance-controlled entries in the compliance ledger, and revoking or clearing associated patient credentials from the hub upon disassociation, expiration, invalidation of an authenticated patient identifier, patient discharge, or patient reassignment, the authenticated patient identifier comprising a wearable bracelet, biometric credential, smart card, mobile device, or electronic patient token.

27. The method of claim 20, further comprising establishing, by at least one routing, gateway, or intermediary communication device deployed within a healthcare facility, patient home, ambulatory setting, or remote-care environment, a bidirectional connection between the hub and institutional systems comprising hospital-information systems, control systems, communication systems, alarm systems, governance systems, or data-management systems, and between the hub and patient-facing systems comprising tablets, mobile devices, software applications, or patient-facing endpoints, over wired, wireless, optical, or hybrid networks using one or more communication standards selected from Ethernet, Wi-Fi, cellular, satellite, optical, Bluetooth Low Energy, Ultra-Wideband, Radio-Frequency Identification, Near-Field Communication, or USB-C communication interfaces; managing, normalizing, and validating data exchanged among the hub, institutional infrastructure, and patient-facing systems; and recording each validated transmission as a compliance-controlled entry in the compliance ledger.

28. A non-transitory computer-readable storage medium storing instructions for operating an integrated clinical infrastructure hub configured for installation within or on a wall of a healthcare environment, the integrated clinical infrastructure hub comprising a power-management subsystem, a modular receptor assembly, a medical-device integration module, an artificial-intelligence execution environment, a patient-facing subsystem, a communication subsystem, a compliance-governance subsystem, and a control unit, the instructions, when executed by at least one processor of the control unit, causing the control unit to:

(a) receive medical-device data from one or more connected medical devices through the medical-device integration module;

(b) receive patient-associated data from the patient-facing subsystem, the patient-associated data being associated with an authenticated patient identifier or an authenticated patient session;

(c) receive operational data from the power-management subsystem, the operational data comprising at least one of voltage data, current data, thermal data, load-state data, power-source status data, or power-quality data;

(d) receive communication-state data from the communication subsystem, the communication-state data comprising at least one of link-state data, network-authentication data, latency data, packet-loss data, routing data, or external-system connection data;

(e) validate, using the compliance-governance subsystem, the medical-device data, the patient-associated data, the operational data, and the communication-state data against one or more compliance policies stored in a policy store;

(f) enforce, using a deny-by-default gate of the compliance-governance subsystem, a default block against release of data, execution of control commands, activation of patient-facing services, artificial-intelligence execution, power-state control, clinical signaling, or external-system communication unless validation succeeds;

(g) generate, refresh, or revoke governance tokens defining authorization conditions for at least one of data exchange, patient-facing service activation, artificial-intelligence execution, medical-device communication, power-state control, clinical signaling, or external-system communication;

(h) cause the artificial-intelligence execution environment to perform local artificial-intelligence inference or rule-based analysis using an artificial-intelligence accelerator module disposed within the hub, or delegate artificial-intelligence execution to a remote computational resource under authorization of a governance token;

(i) record, in a compliance ledger, compliance-controlled entries corresponding to validation events, governance-token events, patient-association events, power-management events, medical-device communication events, artificial-intelligence execution events, clinical-signaling events, and external-communication events; and (j) coordinate operation of the medical-device integration module, the artificial-intelligence execution environment, the patient-facing subsystem, the communication subsystem, and the power-management subsystem through the compliance-governance subsystem so that medical-device integration, patient-facing services, artificial-intelligence execution, communication, and regulated power management are controlled through governance-token authorization, deny-by-default validation, and compliance-ledger recording.

29. The non-transitory computer-readable storage medium of claim 28, wherein the instructions further cause the control unit to synchronize selected compliance-controlled entries of the compliance ledger with one or more additional integrated clinical infrastructure hubs or governance nodes across healthcare, institutional, home-care, ambulatory, or remote-care locations to support distributed validation, cross-site auditability, policy harmonization, inter-facility coordination, regulatory oversight, or longitudinal compliance assurance.

30. The non-transitory computer-readable storage medium of claim 28, wherein the instructions further cause the control unit to revoke or clear patient credentials associated with the patient-facing subsystem upon disassociation, expiration, invalidation of an authenticated patient identifier, patient discharge, or patient reassignment, and to record each credential-revocation or credential-clearing event as a compliance-controlled entry in the compliance ledger.

* * * * *